United States Patent [19]

Okada et al.

[11] Patent Number: 5,674,886
[45] Date of Patent: Oct. 7, 1997

[54] TRIAZOLYLATED TERITIARY AMINE COMPOUND OR SALT THEREOF

[75] Inventors: Minoru Okada; Eiji Kawaminami; Toru Yoden; Masafumi Kudou; Yasuo Isomura, all of Ibaraki, Japan

[73] Assignee: Yamanouchi Pharmaceutical Co., Ltd., Tokyo, Japan

[21] Appl. No.: 199,180

[22] PCT Filed: Aug. 27, 1992

[86] PCT No.: PCT/JP92/01089

§ 371 Date: Feb. 24, 1994

§ 102(e) Date: Feb. 24, 1994

[87] PCT Pub. No.: WO93/05027

PCT Pub. Date: Mar. 18, 1993

[30] Foreign Application Priority Data

Sep. 2, 1991 [JP] Japan .................. 3-248268
Dec. 2, 1991 [JP] Japan .................. 3-344011

[51] Int. Cl.[6] .................. C07D 249/08; A61K 31/41
[52] U.S. Cl. .................. 514/383; 548/264.8; 548/265.4
[58] Field of Search .................. 548/264.8, 265.4; 514/383

[56] References Cited

U.S. PATENT DOCUMENTS 5,041,458 8/1991 Basarab .................. 514/383

FOREIGN PATENT DOCUMENTS 0283245 9/1988 European Pat. Off. .
0324359 7/1989 European Pat. Off. .

OTHER PUBLICATIONS

World Intellectual Property Organization, WO–A–90 14338 (Fisons PLC) 1990.

Primary Examiner—Robert Gerstl
Attorney, Agent, or Firm—Burgess, Ryan & Wayne

[57] ABSTRACT

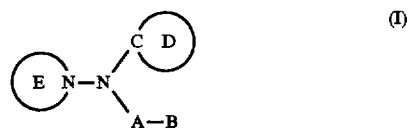

(I)

A triazolylated tertiary amine compound represented by general formula (I) or a salt thereof, having an aromatase inhibitory activity and being useful for preventing and treating breast cancer, mastopathy, endometriosis, prostatomergaly, etc., wherein A represents a single bond, lower alkylene or carbonyl; B represents lower alkyl, aryl, a 5- or 6-membered heterocyclic group, or a bicyclic fused heterocyclic group; D represents aryl, a 5- or 6-membered heterocyclic group, or a bicyclic fused heterocyclic group; and E represents 4H-1,2,4-triazolyl, 1H-1,2,4-triazolyl or 1H-1,2,3-triazolyl.

10 Claims, No Drawings

TRIAZOLYLATED TERITIARY AMINE COMPOUND OR SALT THEREOF

This application is a 371 of PCT/JPA 92/01089 filed Aug. 27, 1992.

TECHNICAL FIELD

The present invention relates to novel triazolyl-substituted tertiary amine compounds having an aromatase inhibiting activity useful as medicines.

BACKGROUND ART

Regarding biosynthesis of estrogen in a living body, it is known that an enzyme, aromatase, participates in the final step of the route of the biosynthesis. Aromatase aromatizes A ring of asteroid with a substrate of androgen to form estrogen. Therefore, by inhibiting this enzyme activity, prevention and curing of various diseases caused by estrogen as an exacerbating factor is possible.

On the basis of this knowledge, some aromatase inhibiting compounds have heretofore been proposed. As typical examples of them, mentioned are imidazolyl- or triazolyl- or pyridyl-substituted methyl compounds described in European Patent Laid-Open Nos. 236,940 and 293,978.

However, compounds of the present invention are structurally different from the known compounds in that the former have a triazolyl-substituted tertiary amino group. Such compounds having a triazolyl-substituted tertiary amino group are not known to have been produced up to the present. In particular, any effective method of direct alkylation, especially arylation, of the terminal amino group of the triazolyl group has not been known.

The present invention provides novel triazolyl-substituted tertiary amino compounds which are structurally different from any known compounds and also provides an optimum method of producing them. In addition, the novel compounds were found to have an excellent aromatase inhibiting activity. On the basis of these findings, the present invention has been completed.

DISCLOSURE OF THE INVENTION

The triazolyl-substituted tertiary amino compounds according to the present invention are represented by the following general formula (I):

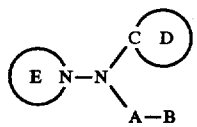

(I)

wherein A represents a single bond, a lower alkylene group or a carbonyl group;

B represents a lower alkyl group, an optionally substituted aryl group, an optionally substituted 5- or 6-membered heterocyclic group having from 1 to 3 hetero atoms of oxygen, sulfur and/or nitrogen atoms, or an optionally substituted bicyclic fused heterocyclic group composed of the preceding hetero ring and a benzene ring; D ring represents an optionally substituted aryl group, an optionally substituted 5- or 6-membered heterocyclic group having from 1 to 3 hetero atoms of oxygen, sulfur and/or nitrogen atoms, or an optionally substituted bicyclic fused heterocyclic group composed of the preceding hetero ring and a benzene ring; and E ring represents a 4H-1,2,4-triazole ring, a 1H-1,2,4-triazole ring or a 1H-1,2,3-triazole ring. These definitions apply hereinafter.

Compounds of the present invention will be explained in more detail hereinafter. The term "lower" as used herein indicates a linear or branched carbon chain having from 1 to 6 carbon atoms, unless otherwise specifically defined.

Therefore, a "lower alkyl group" concretely includes, for example, a methyl group, an ethyl group, a propyl group, an isopropyl group, a butyl group, an isobutyl group, a sec-butyl group, a tert-butyl group, a pentyl (amyl) group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, and a 1-ethyl-2-methylpropyl group. Of them, preferred are a methyl group, an ethyl group, a propyl group, an isopropyl group and a butyl group.

A "lower alkylene group" is a linear or branched carbon chain having from 1 to 6 carbon atoms, concretely including, for example, a methylene group, an ethylene group, a propylene group, a tetramethylene group, a 2-methyltrimethylene group, a 1-ethylethylene group, a pentamethylene group, and a 1,2-diethylethylene group. Of them, preferred are a methylene group and an ethylene group.

The "aryl group" for B or D ring includes, for example, a phenyl group, a naphthyl group, an anthracenyl group and a phenanthrenyl group; and the "5- or 6-membered heterocyclic group having from 1 to 3 hetero atoms of oxygen, sulfur and/or nitrogen atoms" for the ring includes, for example, a furyl group, a thienyl group, a thiazolyl group, a thiadiazolyl group, an oxazolyl group, an imidazolyl group, a triazolyl group, a pyrrolyl group, a pyridyl group, a pyrimidinyl group, and a pyradinyl group. The "bicyclic fused heterocyclic group composed of the preceding hetero ring and a benzene ring" includes, for example, a benzothiazolyl group, a benzoxazolyl group, a quinolyl group, an isoquinolyl group, a benzotriazolyl group, and a benzofurazanyl group.

The above-mentioned "aryl group", "5- or 6-membered heterocyclic group having from 1 to 3 hetero atoms of oxygen, sulfur and/or nitrogen atoms", and "bicyclic fused heterocyclic group composed of the preceding hetero ring and a benzene ring" each may have one or more, preferably 1 or 2, substituents.

As examples of substituents for the groups, there are mentioned a halogen atom, a cyano group, a nitro group, a trifluoromethyl group, a hydroxyl group, an amino group, a mono- or di-lower alkylamino group, a lower alkyl group, a lower alkoxy group, a carboxyl group, a lower alkoxycarbonyl group, a lower alkanoyl group, a lower alkanoyloxy group, a lower alkanoylamino group, an aroyl group, an aroyloxy group, a carbamoyl group, a mono- or di-lower alkylaminocarbonyl group, a sulfonic acid group, a lower alkylsulfonyl group, a sulfamoyl group, and a mono- or di-lower alkylsulfamoyl group. Of them, preferred are a halogen atom, a cyano group, a nitro group, a trifluoromethyl group, a hydroxyl group, an amino group, a lower alkyl group, a lower alkoxy group, a carboxyl group, a lower alkoxycarbonyl group, and a lower alkanoylamino group. More preferred are a halogen atom, a cyano group and a nitro group.

The "halogen atom" includes a fluorine atom, a chlorine atom, a bromine atom and an iodine atom. The "lower alkoxy group" includes a methoxy group, an ethoxy group, a propoxy group, an isopropoxy group, a butoxy group, an isobutoxy group, a sec-butoxy group, a tert-butoxy group, a pentyloxy (amyloxy) group, an isopentyloxy group, a tert-pentyloxy group, a neopentyloxy group, a 2-methylbutoxy group, a 1,2-dimethylpropoxy group, a 1-ethylpropoxy group, and a hexyloxy group. Of them, preferred are a methoxy group and an ethoxy group.

The "lower alkoxycarbonyl group" includes a methoxycarbonyl group, an ethoxycarbonyl group, a propoxycarbonyl group, a butoxycarbonyl group, a tert-butoxycarbonyl group, and a pentyloxycarbonyl group; the "lower alkanoyl (oxy) group" includes an acetyl(oxy) group, a propionyl (oxy) group, a butyryl(oxy) group, a valeryl(oxy) group, and an isovaleryl(oxy) group; and the "lower alkanoylamino group" includes an acetylamino group, a propionylamino group, a butyrylamino group, valerylamino group, and an isovalerylamino group.

The "aroyl group" or "aroyloxy group" includes a benzoyl (oxy) group, a 1-naphthylcarbonyl(oxy) group, a 2-naphthylcarbonyl(oxy) group, a thienoyl(oxy) group, a pyrroloyl(oxy) group, and a 2-, 3- or 4-pyridylcarbonyl-(oxy) group.

The meaning of the above-mentioned "lower alkyl group" shall apply to the lower alkyl moiety in the "mono- or di-lower alkylaminocarbonyl group" or the "mono- or di-lower alkylsulfamoyl group". Typical examples of the groups are a methylaminocarbonyl group, a dimethylaminocarbonyl group, a diethylaminocarbonyl group, a propylaminocarbonyl group, a methylsulfamoyl group, a dimethylsulfamoyl group, and a diethylaminosulfamoyl group.

The "lower alkylsulfonyl group" includes a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, and a hexylsulfonyl group.

The compounds of the present invention may easily form salts with inorganic acids or organic acids, and the salts also have an aromatase inhibiting activity like the corresponding free bases. As preferred salts, for example, mentioned are inorganic acid salts such as hydrochlorides, hydrobromides, sulfates, nitrates and phosphates; as well as organic acid salts such as oxalates, fumarates and tartarates.

Depending upon the kinds of the substituents in the compounds, the compounds may also form pharmaceutically acceptable salts with alkali metals or alkaline earth metals (e.g., sodium, potassium, magnesium or calcium salts) or form salts with organic amines such as ammonia or triethylamine.

Depending upon the kinds of the substituents in the compounds, the compounds may have an asymmetric carbon atom and they include all isomers such as optical isomers and diastereomers based on the asymmetric carbon atom.

In addition, there are various hydrates, solvates and tautomers of the compounds of the present invention, as the case may be. The present invention also includes the isolated hydrates, solvates or tautomers as well as mixtures of them.

The compounds of the present invention can be produced by various methods, on the basis of the characteristics of the basic skeleton thereof and also those of the kinds of the substituents therein. Some typical methods are mentioned below.

First Production Method:

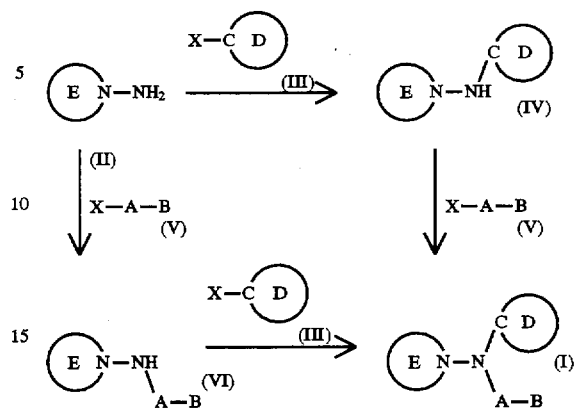

wherein X represents a halogen atom, an arylsulfonyloxy group, or a lower alkylsulfonyloxy group.

Production of the intended compound (I) from an N-aminotriazole (II) may be effected by the above-mentioned two routes. The reaction in each step in the routes is alkylation or acylation of the amino group, which may be conducted in the same manner.

Specifically, in accordance with the above-mentioned reaction, reaction-corresponding amounts of starting compounds are brought into contact with each other, for example, in a solvent which is inert to the reaction, such as dimethylformamide, dimethylsulfoxide, tetrahydrofuran, dimethoxyethane, acetone or methyl ethyl ketone, in the presence of a base. As the base, usable are, for example, sodium hydride, sodium amide, n-butyl lithium, potassium t-butoxide, sodium, sodium methoxide, sodium ethoxide, sodium hydroxide and potassium hydroxide. The reaction may be effected with ease at room temperature.

The arylsulfonyloxy group in this case includes, for example, a phenylsulfonyloxy group and a benzylsulfonyloxy group; and the lower alkylsulfonyloxy group is a sulfonyloxy group substituted by a lower alkyl group, including, for example, a methylsulfonyloxy group, an ethylsulfonyloxy group and a propylsulfonyloxy group.

Second Production Method:

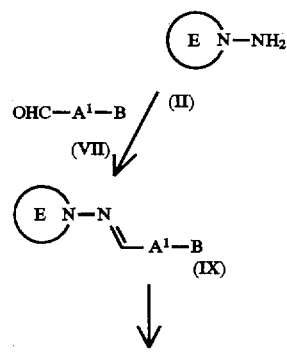

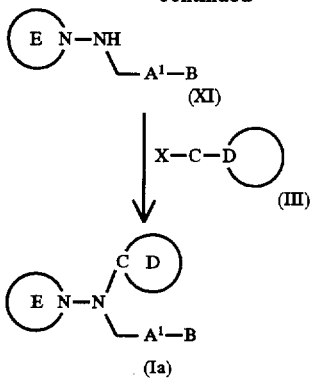

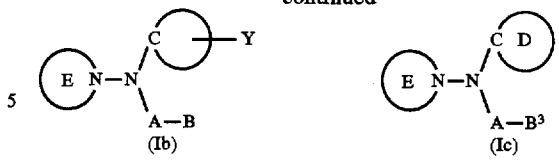

wherein $A^1$ represents a lower alkylene group in which the number of methylene groups is smaller than A by one. The same definition applies hereinafter.

In accordance with the method, an N-aminotriazole (II) is reacted with an aldehyde compound (VII) to give the corresponding Schiff base (IX), this base (IX) is reduced to give a compound (XI), and the compound (XI) is alkylated or acylated in the same manner as in the first production method to obtain the intended product (Ia). The reaction of forming the Schiff base is effected by azeotropic dehydration or the like, in a solvent, such as methanol, ethanol or the like alcohol or benzene or toluene, in the presence of an acid catalyst. The reduction may be effected by an ordinary method, using, for example, sodium borohydride, lithium borohydride or sodium borocyanide hydride. As the reaction solvent, usable is an alcohol such as methanol or ethanol, or an organic solvent such as acetic acid, or water, or a mixed solvent of them. In the reduction, the Schiff base formed may not be isolated but a reducing agent may be added to the Schiff base-containing reaction solution to conduct the reduction.

Third Production Method:

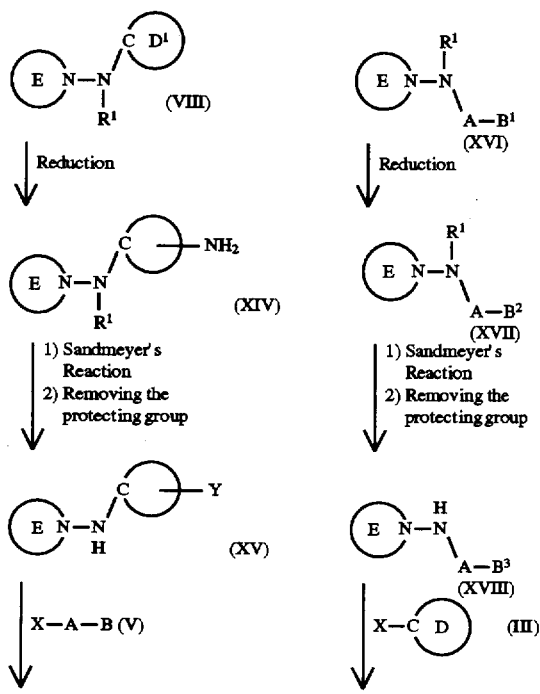

wherein $R^1$ represents an amino-protecting group; Y represents a halogen atom; $B^I$ and $D^I$ each represent an aryl group, a 5-membered or 6-membered heterocyclic group or a bicyclic fused heterocyclic group composed of the preceding hetero ring and a benzene ring, which is substituted by a nitro group; $B^2$ represents an aryl group, a 5-membered or 6-membered heterocyclic group or a bicyclic fused heterocyclic group composed of the preceding hetero ring and a benzene ring, which is substituted by an amino group; and $B^3$ represents an aryl group, a 5-membered or 6-membered heterocyclic group or a bicyclic fused heterocyclic group composed of the preceding hetero ring and a benzene ring, which is substituted by a halogen atom. These definitions apply hereinafter.

In accordance with the method, halogen-substituted compounds of a general formula (Ib) or (Ic) of the present invention are obtained.

Thus, a compound of a general formula (XIII) or (XVI) is reduced to give an amino compound of a general formula (XIV) or (XVII); the amino compound is subjected to Sandmeyer's reaction where a halogen atom is introduced and the protecting group is removed, to give a compound of a general formula (XV) or (XVIII), and this compound is reacted with a compound (V) or (III) to give the intended compound (Ib) or (Ic), respectively.

Reduction of the compound of formula (XIII) is effected by an ordinary method of chemical reduction or catalytic reduction.

As a reducing agent to be used in chemical reduction, suitable are metals such as tin, zinc or iron. As catalytic reduction, conventional catalysts are used, including, for example, a platinum catalyst such as platinum or platinum oxide, a palladium catalyst such as palladium black or palladium oxide, and a nickel catalyst such as Raney nickel.

As a solvent for the reduction reaction, any conventional solvent can be used, including, for example, methanol, ethanol, propanol, ethyl acetate and acetic acid. Protection of the nitrogen atom of the compound of formula (XIII) or (XVI) is effected with a conventional acyl-protecting group such as acetyl or benzoyl group. Introduction of the protecting group may be effected by reaction of the compound with acetic anhydride, acetyl chloride or benzoyl chloride, in the presence of a base such as sodium acetate, pyridine, picoline, lutidine, trimethylamine or triethylamine. As a solvent for the reaction, usable are dichloromethane, dichloroethane, chloroform, benzene or toluene. The reaction may also be effected in the absence of a solvent.

Next, the thus obtained compound (XIV) or (XVII) is subjected to Sandmeyer's reaction so that a halogen atom is introduced thereinto and then the protecting group is removed to yield a compound (XV) or (XVIII). Sandmeyer's reaction may be effected by any ordinary method, for example, using cuprous chloride, cuprous bromide or cuprous iodide and hydrochloric acid, hydrobromic acid, hydroiodic acid or sulfuric acid. As a solvent for the reaction, usable are water, acetone, dioxane, and tetrahydrofuran. Removal of the protecting group may be effected by acid hydrolysis with dilute hydrochloric acid or dilute sulfuric acid. To the reaction of the thus obtained compound (XV) and a compound (V) or (III), the same way as mentioned in the first production method and the second production method may apply.

Other Production Methods:

(1) Where the compounds of the present invention has an amino group as a substituent, they are obtained by reducing the compound of the present invention having a corresponding nitro group. The reaction is conversion of a substituent, to which the same reduction as that in the third method may apply.

(2) Where the compounds of the present invention has a lower alkanoylamino group as a substituent, they may be obtained by reacting the compound of the present invention having a corresponding amino group with acetic anhydride or the like by an ordinary method.

(3) Where the compounds of the present invention has a benzotriazole group in the substituent B or as the ring D, they may be obtained by reducing the compound of the present invention having an amino group (or a monosubstituted amino group) and a nitro group as the adjacent substituents in the phenyl group, at the nitro group to convert it into an amino group, followed by reacting the reduced compound with sodium nitrite, potassium nitrite or the like to effect ring closure to form a benzotriazole group in the compound.

The compounds of the present invention thus prepared can be isolated and purified by any conventional methods, for example, by extraction, precipitation fractional chromatography, fractional crystallization, recrystallization or the like. Salts of the compounds of the present invention can be produced by subjecting the free base to ordinary salt-forming reaction to give a desired salt thereof.

Industrial Applicability

The compounds of the present invention have a function of inhibiting an aromatase, which participates in estrogen biosynthesis from androgen. Therefore, the compounds of the present invention are useful for treatment of the diseases in which estrogen participates as an exacerbating factor, such as breast cancer, mastopathy, endometriosis, prostatomegaly, hysteromyoma, and cancer of uterine body.

References:
 Pharmacia, 26 (6) 558 (1990);
 Clinical Endocrinology, 32 623 (1990);
 J. Steroid Biochem. Molec. Biol., 37 (3) 335 (1990);
 Br. J. Cancer, 60 5 (1989);
 Endocrinology, 126. (6) 3263 (1990);
 The Journal of Pharmacology and Experimental Therapeutics, 244 (2) (1988);
 Endocrinol. Japan, 37 (5) 719 (1990);
 Steroids, 50 1 (1987).

Experimental Methods:

Pharmacological effects of the compounds of the present invention were identified by the methods mentioned below.

(1) In vitro inhibition of aromatase:
  (a) Inhibition of aromatase obtained from rat ovary:
    The activity was measured in accordance with the method described in J. Biol. Chem., 249 5364 (1974).
    The $IC_{50}$ value of the test compound on aromatase inhibition was determined based on inhibition of $^3H_2O$ to be released from [1,2-$^3$H] androstenedione in rat ovarian microsomes.
  (b) Inhibition of aromatase obtained from human placenta
    The activity was measured in accordance with the method described in Endocrine Research, 16 (2) 253 (1990).
    The inhibition activity of the compound was determined based on the inhibition of $^3H_2O$ to be released from [1,2-$^3$H] androstenedione in human placenta microsomes.

(2) In vivo inhibition of aromatase activity
  To female Wister rats each weighing 60 g (not matured), were injected subcutaneously 100 IU/rat of mare's serum gonadotropin (PMSG). After 72 hours, a test compound dissolved in 0.5 ml of a 20% polyethylene glycol aqueous solution was administered to the rat. As a control, a 20% polyethylene aglycol aqueous solution was administered. Three hours after the administration, the rats were sacrificed by decapitation and bleeding and their ovaries were removed and the estradiol content of the ovaries were measured by RIA.

(3) Antitumor activity:
  The antitumor activity of a test compound to breast carcinoma was measured in a dimethylbenzanthracene (DMBA)-induced female Sprague-Dawlay rat tumor.

(4) In vitro and in vivo inhibition of aldosterone production:
  (a) In vitro inhibition of aldosterone production:
    The activity was measured in accordance with the method described in J. Vet. Pharmacol. Therap., 11 345 (1988). The inhibition activity of the test compound was determined based on the inhibition of aldosterone production produced by stimulation of first-generation of rat adrenal cultured cells by ACTH. The amount of aldosterone was measured by RIA.
  (b) In vivo inhibition of aldosterone production in rats:
    The inhibitory activity was measured in accordance with the method described in J. Steroid Biochem., 34 567 (1989). The inhibitory activity of a test compound was determined based on inhibition of the blood aldosterone to be increased by stimulation by ACTH in rats. The amount of aldosterone was measured by RIA.

(5) In vitro inhibition of cortisol production:
  The inhibitory activity was measured in accordance with the method described in Endocrinology, 114 (2) 486 (1984). The inhibitory activity of a test compound was determined based on inhibition of the cortisol production produced by stimulation of first-generation of rabit adrenal cultured cells by ACTH. The amount of cortisol was measured by RIA.

Results of Experiments:

The results of the experiments mentioned above are shown below.

1. In vitro inhibition of aromatase in human placenta microsomes:
  Activity
  $IC_{50}$ value for ex vivo inhibition of aromatase from human placental microsomes was obtained in accordance with the above-mentioned experimental method (1-b), and the results obtained are shown in Table 1.

TABLE 1

| Test Compound | $IC_{50}$ |
|---|---|
| Compound of Example 10 | 0.11 nM |
| Compound of Example 12 | 0.03 nM |
| Compound of Example 15 | 0.13 nM |
| Control Compound | 0.41 nM |

Control Compound: Compound of Example 20 (b) in European Patent Laid-Open No. 236,940. The same shall apply hereinafter.

As is obvious from the results above, the compounds of the present invention exhibited a significantly higher in vitro inhibition of aromatase in human placental microsomes than the control compound.

2. Selectivity of In vitro inhibition of rat ovarian aromatase and in vitro aldosterone production in rat:

$IC_{50}$ values for in vitro inhibition of rat aromatase and ex vivo inhibition of rat aldosterone production were measured in accordance with the above-mentioned experimental methods (1-a) and (4-a), respectively. The selectivity was obtained by calculation and shown in Table 2. The selectivity indicates a ratio of $IC_{50}$ value for rat aldosterone production to $IC_{50}$ value for rat aromatase.

TABLE 2

| Test Compound | $IC_{50}$ of Compound of Example 15 | Control Compound |
|---|---|---|
| Rat aromatase inhibitory activity (A) | 0.37 nM | 1.83 nM |
| Rat aldosterone inhibitory activity (B) | 2.25 nM | 3.18 nM |
| Selectivity (B/A) | 6100 | 1700 |

As is obvious from the results above, the compound of the present invention also exhibited a significantly higher rat aromatase in vitro inhibitory activity than the control compound. In addition, both compounds exhibited almost the same in vitro rat aldosterone production inhibitory activity.

Therefore, the selectivity of the in vitro aromatase inhibitory activity to the in vitro aldosterone production inhibitory activity (B/A) of the compound of Example 15 of the present invention was 6100, and that of the control compound was 1700. This means that the compound of the present invention has an extremely small influence on the aldosterone producing system and therefore is a highly selective aromatase inhibitor.

Aldosterone which is known as a mineral corticoid has some biological effects. It is known that inhibition of aldosterone production causes some harmful side effect, such as depression of blood pressure and orthostatic hypotension due to decrease of the body fluid as well as abnormal electrolyte balance by lost of potassium ions form the body. Accordingly, since the compound of the present invention is an aromatase inhibitor with high enzyme selectivity with less inhibition activity of aldosterone production, it is expected to be a highly safe compound with few harmful side effects.

3. In vivo inhibition of aldosterone production in rats:

By the above-mentioned experimental method (4-b), aldosterone production inhibitory activity in rats was measured. Where 10 mg/kg of the test compound was administered to each of five rats, inhibition of the aldosterone production in the rats was 37%, which is significant in comparison with the control.

On the other hand, where 100 mg/kg (10 times of the above case) of each of the compounds of Examples 10, 12 and 15 of the present invention was administered to each of five rats (as test group), they did not inhibit aldosterone production significantly. The statistical significance of value was analyzed by using one-way ANOVA. The results mean that the compounds of the present invention are highly safe compounds with few harmful side effects also in the in vivo test as well.

4. In vitro inhibition of cortisol production in rabbit:

$IC_{50}$ value of the compounds for in vitro inhibition of cortisol production was obtained by the above-mentioned experimental method (5), and the results obtained are shown in Table 3.

TABLE 3

| Test Compound | $IC_{50}$ |
|---|---|
| Compound of Example 10 | 7.0 µM |
| Compound of Example 15 | 4.0 µM |
| Control Compound | 1.6 µM |

As is obvious from the results above, it is noted that the compounds of the present invention exhibited a significantly lower in vitro cortisol production inhibitory activity in rabbit than the control compound. It is known that the inhibition of cortisol production causes various harmful side effects such as depression of blood sugar, nervous system function disorders, increase of stress and increase of inflammation. Accordingly, since the compounds of the present invention have a weak cortisol inhibiting activity, they are expected to be compounds having less harmful side effects than the control compound.

5. In vivo inhibition of aromatase activity:

Aromatase activity inhibitory activity in rat was measured by the above-mentioned experimental method (2). The minimum effective dose of the compound of the present invention was 0.001 mg/kg.

6. Antitumor activity:

In accordance with the above-mentioned experimental method (3), compounds of the present invention cause suppression or regression of existing tumors at daily oral doses of about 0.04 to 1.0 mg/kg.

7. Metabolism:

Where 3 mg/kg of the compound of Example 15 of the present invention was orally administered to test rats, the maximum value (Cmax) of the concentration of the non-changed compound in the plasma was 2.88 µg/ml and the extinction half time $(T_{1/2})$ was 11 hours. From the results, it is understood that the compound of the present invention has an excellent oral absorbability and that the effect of the absorbed compound lasts long. Thus, the compound has a good profile as a medicine.

Where the compounds of formula (I) and their non-toxic salts or hydrates are used for the above-mentioned objects, they are generally administered orally or parenterally. The amount employed for dose varies, in accordance with the age, body weight and condition of patients, as well as the curing effect, administration route and treating time with the compounds. In general, it is from 0.1 to 100 mg/adult/day, preferably from 1 to 10 mg/adult/day, for oral administration all at one time or in smaller doses for several administrations a day; or from 0.1 to 100 mg/adult/day for parenteral administration all at one time or in smaller doses for several administrations or for continuous intravenous injection for from 1 to 24 hours a day. Since the amount of the compounds of the present invention for dose varies, depending upon various conditions, a smaller dose than the range defined above would often be satisfactory in some cases.

As a solid composition for peroral administration of the present invention, usable are tablets, powder and granules. In the solid composition of the kind, one or more active substances are blended with at least one inert diluent, such as lactose, mannitol, glucose, hydroxypropyl cellulose, fine crystalline cellulose, starch, polyvinyl pyrrolidone and magnesium aluminate metasilicate. The composition may optionally contain any other additives than the inert diluent, for example, disintegrator such as magnesium stearate, disintegrator such as calcium glycolate cellulose, a stabilizer such as lactose, and a dissolution aid such as glutamic acid or aspartic acid, by an ordinary method. Tablets and pills may optionally be coated with a film of a gastric-soluble or enteric-soluble substance, such as sucrose, gelatin, hydroxypropyl cellulose or hydroxypropylmethyl cellulose phthalate.

A liquid composition for oral administration of the present invention includes pharmaceutically acceptable emulsion, solution, suspension, syrup and elixir and it contains a conventional inert diluting agent such as pure water or ethanol. The composition may further contain, in addition to the inert diluting agent, other auxiliary agents such as a wetting agent or a suspending agent, as well as a sweetener, a flavor, an aroma and an antiseptic agent.

An injection for parenteral administration of the present invention includes sterilized aqueous or non-aqueous solution, suspension and emulsion. The aqueous solution and suspension contain, for example, an injectable distilled water and a physiological saline. The non-aqueous solution and suspension contain, for example, propylene glycol, polyethylene glycol, vegetable oils such as olive oil, alcohols such as ethanol, and Polysorbate 80, etc. The composition of the kind may further contain other auxiliary additives such as an antiseptic agent, a wetting agent, an emulsifier, a dispersing agent, a stabilizer (e.g., lactose), a dissolution aid (e.g., glutamic acid, aspartic acid), etc. The composition is sterilized, for example, by filtration through a bacteria-retaining filter, by incorporation of a microbicide thereto, or by light irradiation. As the case may be, a sterilized solid composition is first prepared, and it may be dissolved in a sterilized water or sterilized injectable solvent to give an injection before use.

BEST MODE FOR CARRYING OUT THE INVENTION

Next, the present invention will be explained in more detail by way of the following examples. Preparation of the starting compounds to be used in the examples is disclosed as referential examples.

REFERENTIAL EXAMPLE 1

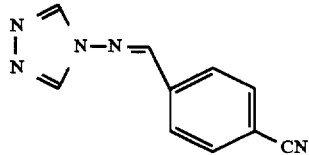

80 Milliliters of benzene was added to 8.4 g of 4-amino-1,2,4-triazole, 13.1 g of p-cyanobenzaldehyde and 1.9 g of p-toluenesulfonic acid monohydrate and the mixture was heated under reflux for 4 hours under azeotropic dehydration condition. After cooled, the crystals as precipitated out were taken out by filtration to quantitatively obtain 4-[(4-cyanobenzylidene)amino]-4H-1,2,4-triazole.

Mass Spectrometry (m/z): 198 (M⁺+1)

REFERENTIAL EXAMPLE 2

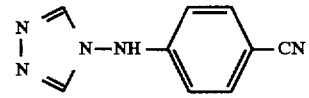

2.52 Grams of 4-amino-1,2,4-triazole was added little by little to a dimethylsulfoxide suspension of 1.2 g of sodium hydride at room temperature. After stirred for 3 hours at room temperature, 1.21 g of 4-fluorobenzonitrile was added thereto all at a time, and stirring was continued for further one hour. Water was added to the reaction solution, and the mixture was then extracted with ethyl acetate. The organic layer was dried over anhydrous magnesium sulfate, and the solvent was removed by distillation under reduced pressure. The crystals obtained were washed with ethyl acetate to give 1.09 g of 4-[(4-cyanophenyl)amino]-4H-1,2,4-triazole.

Nuclear Magnetic Resonance Spectrum (DMSO-$d_6$, TMS internal standard)

δ: 6.57 (2H, d, J=9 Hz), 7.69 (2H, d, J=9 Hz), 8.83 (2H, s)

Mass Spectrometry (m/z): 185 (M⁺)

REFERENTIAL EXAMPLE 3

In the same manner as in Referential Example 2, the following compound was obtained.

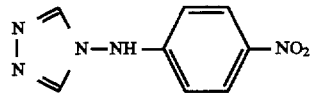

4-[(4-Nitrophenyl)amino]-4H-1,2,4-triazole

Starting Compounds: 4-amino-1,2,4-triazole and 4-fluoronitrobenzene

Nuclear Magnetic Resonance Spectrum (DMSO-$d_6$, TMS internal standard)

δ: 6.53–6.70 (2H, m), 8.08–8.31 (2H, m), 8.88 (2H, s), 10.52 (1H, s)

Mass Spectrometry (m/z): 205 (M⁺)

REFERENTIAL EXAMPLE 4

In the same manner as in Referential Example 2, the following compound was obtained.

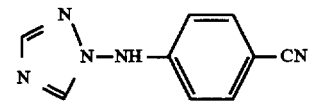

1-[(4-Cyanophenyl)amino]-1H-1,2,4-triazole

Starting Compounds: 1-amino-1,2,4-triazole and 4-fluorobenzonitrile

Nuclear Magnetic Resonance Spectrum (DMSO-$d_6$, TMS internal standard)

δ: 6.56 (2H, d, J=9 Hz), 7.70 (2H, d, J=9 Hz), 8.18 (1H, s), 8.82 (1H, s), 10.51 (1H, brs)

Mass Spectrometry (m/z): 185 (M⁺)

REFERENTIAL EXAMPLE 5-1

In the same manner as in Referential Example 2, the following compound was obtained.

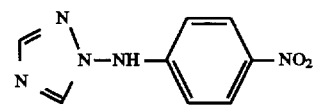

1-[(4-Nitrophenyl)amino]-1H-1,2,4-triazole Starting Compounds: 1-amino-1,2,4-triazole and 4-fluoronitrobenzene Nuclear Magnetic Resonance Spectrum (DMSO-$d_6$, TMS internal standard)

δ: 6.59 (2H, d, J=9 Hz), 8.16 (2H, d, J=9 Hz), 8.20 (1H, s), 8.85 (1H, s), 10.80 (1H, s)

Mass Spectrometry (m/z): 205 (M⁺)

REFERENTIAL EXAMPLE 5-2

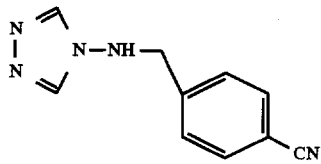

2.28 Grams of sodium borohydride was added gradually to a suspension of 9.85 g of 4-[(4-cyanobenzylidene)amino]-4H-1,2,4-triazole obtained in Referential Example 1 in 100 ml methanol under ice-cooling. The reaction mixture was stirred at the same temperature for 1 hour, and the solvent was removed by distillation under reduced pressure. Water and sodium chloride were added to the residue successively for salting-out, and the mixture was extracted with ethyl acetate. The organic layer was dried over anhydrous magnesium sulfate, and the solvent was removed by distillation under reduced pressure. The residue was subjected to silica gel column chromatography, and crude crystals from the chloroform/methanol (15:1) eluate were washed with chloroform to give 4.2 g of 4-[(4-cyanobenzyl)amino]-4H-1,2,4-triazole.

Physicochemical properties:

Mass Spectrometry (m/z): 199 (M⁺)

Nuclear Magnetic Resonance Spectrum (DMSO-$d_6$, TMS internal standard)

δ: 4.31 (2H, d, J=4 Hz), 7.29 (1H, t, J=4 Hz), 7.51 (2H, d, J=9 Hz), 7.82 (2H, d, J=9 Hz), 8.48 (2H, s)

EXAMPLE 1

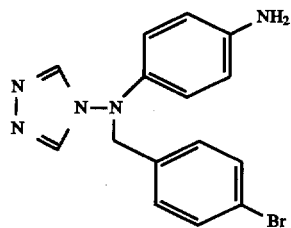

A catalytic amount of Raney nickel was added to 50 ml of an ethanol solution containing 3.74 g of 4-[N-(4-bromobenzyl)-N-(4-nitrophenyl) amino]-4H-1,2,4-triazole, and the mixture was stirred for about 2 hours in the presence of hydrogen gas at room temperature. After the catalyst was removed by filtration, the resulting filtrate was concentrated under reduced pressure and the residue was purified by silica gel column chromatography to give 1.1 g of 4-[N-(4-aminophenyl)-N-(4-bromobenzyl)amino]-4H-1,2,4-triazole from the chloroform/methanol (50:1) eluate.

Mass Spectrometry (m/z): 344 (M⁺)

Nuclear Magnetic Resonance Spectrum (DMSO-$d_6$, TMS internal standard)

δ: 4.71 (2H, s), 4.98 (2H, br), 6.52 (2H, d, J=9 Hz), 6.85 (2H, d, J=9 Hz), 7.26 (2H, d, J=9 Hz), 7.48 (2H, d, J=9 Hz), 8.73 (2H, s)

EXAMPLE 2

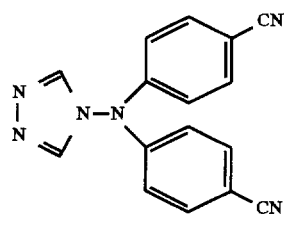

0.3 Gram of 4-[(4-cyanophenyl)amino]-4H-1,2,4-triazole obtained in Referential Example 2 was added little by little to a suspension of 65 mg of sodium hydride in 5 ml of N,N-dimethylformamide at room temperature. After completion of the addition, the reaction mixture was stirred at 50° C. for 30 minutes and then cooled. 5 Milliliters of an N,N-dimethylformamide solution containing 0.20 g of 4-fluorobenzonitrile was added dropwise thereto. After addition, the reaction mixture was stirred at 100° C. for 5 hours, and the solvent was removed by distillation under reduced pressure. Water was added to the residue, and the mixture was then extracted with chloroform. The chloroform layer was washed with water and dried over anhydrous magnesium sulfate, and the solvent was removed by distillation. The residue was purified by silica gel column chromatography, and crude crystals were obtained from the chloroform/methanol (100:1) eluate.

These crude crystals were recrystallized from ethyl acetate to give 0.28 g of 4-[bis(4-cyanophenyl)-amino]-4H-1,2,4-triazole.

Elementary Analysis (for $C_{16}H_{10}N_6$)

|  | C (%) | H (%) | N (%) |
|---|---|---|---|
| Calculated: | 67.13 | 3.52 | 29.35 |
| Measured: | 66.92 | 3.62 | 29.23 |

Mass Spectrometry (m/z): 286 (M⁺)

Nuclear Magnetic Resonance Spectrum (CDCl₃, TMS internal standard)

δ: 7.04 (4H, d, J=9 Hz), 7.69 (4H, d, J=9 Hz), 8.44 (2H, s)

EXAMPLE 3

In the same manner as in Example 2, the following compound was obtained.

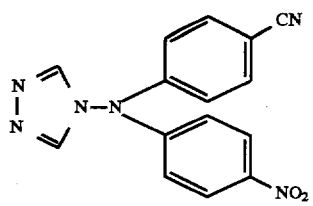

4-[N-(4-cyanophenyl)-N-(4-nitrophenyl)amino]-4H-1,2,4-triazole

Starting Compounds: 4-[(4-cyanophenyl)amino]-4H-1,2,4-triazole and 4-fluoronitrobenzene Elementary Analysis (for $C_{15}H_{10}N_6O_2$)

| | C (%) | H (%) | N (%) |
|---|---|---|---|
| Calculated: | 58.82 | 3.29 | 27.44 |
| Measured: | 58.79 | 3.46 | 27.37 |

Mass Spectrometry (m/z): 307 (M⁺+1)
Nuclear Magnetic Resonance Spectrum (CDCl₃, TMS internal standard)

δ: 6.98–7.16 (4H, m), 7.72 (2H, d, J=9 Hz), 8.26 (2H, d, J=9 Hz), 8.46 (2H, s)

EXAMPLE 4

In the same manner as in Example 2, the following compound was obtained.

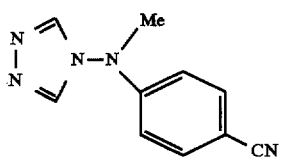

4-[N-(4-cyanophenyl)-N-methylamino]-4H-1,2,4-triazole
Starting Compounds: 4-[(4-cyanophenyl)amino]-4H-1,2,4-triazole and methyl iodide
Elementary Analysis (for $C_{10}H_9N_5$)

| | C (%) | H (%) | N (%) |
|---|---|---|---|
| Calculated: | 60.29 | 4.55 | 35.15 |
| Measured: | 60.24 | 4.66 | 35.12 |

Mass Spectrometry (m/z): 199 (M⁺)
Nuclear Magnetic Resonance Spectrum (CDCl₃, TMS internal standard)

δ: 3.56 (3H, s), 6.60 (2H, d, J=9 Hz), 7.60 (2H, d, J=9 Hz), 8.41 (2H, s)

EXAMPLE 5

In the same manner as in Example 2, the following compound was obtained.

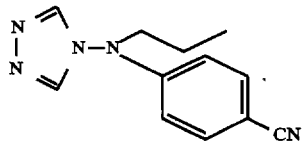

4-[N-(4-cyanophenyl)-N-propylamino]-4H-1,2,4-triazole
Starting Compounds: 4-[(4-cyanophenyl)amino]-4H-1,2,4-triazole and methyl iodide
Elementary Analysis (for $C_{12}H_{13}N_5$)

| | C (%) | H (%) | N (%) |
|---|---|---|---|
| Calculated: | 63.42 | 5.77 | 30.82 |
| Measured: | 63.41 | 5.82 | 30.77 |

Mass Spectrometry (m/z): 227 (M⁺), 198
Nuclear Magnetic Resonance Spectrum (CDCl₃, TMS internal standard)

δ: 1.03 (3H, t, J=7 Hz), 1.45–1.76 (2H, m), 3.67 (2H, dd, J=7 Hz, J=7 Hz), 6.54 (2H, d, J=9 Hz), 7.56 (2H, d, J=9 Hz), 8.33 (2H, s)

EXAMPLE 6

In the same manner as in Example 2, the following compound was obtained.

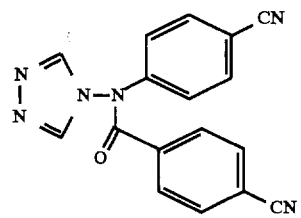

4-Cyano-N-(4-cyanophenyl)-N-(4H-1,2,4-triazol-4-yl)-benzamide
Starting Compounds: 4-[(4-cyanophenyl)amino]-4H-1,2,4-triazole and 4-cyanobenzoyl chloride
Elementary Analysis (for $C_{17}H_{10}N_6O$)

| | C (%) | H (%) | N (%) |
|---|---|---|---|
| Calculated: | 64.96 | 3.21 | 26.74 |
| Measured: | 64.81 | 3.35 | 26.72 |

Mass Spectrometry (m/z): 314 (M⁺)
Nuclear Magnetic Resonance Spectrum (DMSO-d₆, TMS internal standard)

δ: 7.61 (2H, d, J=9 Hz), 7.77–7.99 (6H, m), 9.13 (2H, s)

EXAMPLE 7

In the same manner as in Example 2, the following compound was obtained.

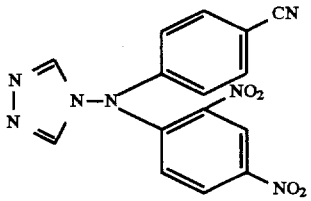

4-[N-(4-cyanophenyl)-N-(2,4-dinitrophenyl)amino]-4H-1,2,4-triazole
Starting Compounds: 4-[(4-cyanophenyl)amino]-4H-1,2,4-triazole and 2,4-dinitrofluorobenzene
Elementary Analysis (for $C_{14}H_9N_7O_6$)

| | C (%) | H (%) | N (%) |
|---|---|---|---|
| Calculated: | 45.29 | 2.44 | 26.41 |
| Measured: | 45.25 | 2.55 | 26.40 |

Mass Spectrometry (m/z): 371 (M⁺)
Nuclear Magnetic Resonance Spectrum (DMSO-d₆, TMS internal standard)

δ: 6.82 (2H, d, J=9 Hz), 7.95 (1H, d, J=9 Hz), 8.20 (2H, d, J=9 Hz), 8.71 (1H, q, J=9 Hz), 8.95 (1H, d, J=3 Hz), 9.21 (2H, s)

EXAMPLE 8

In the same manner as in Example 2, the following compound was obtained.

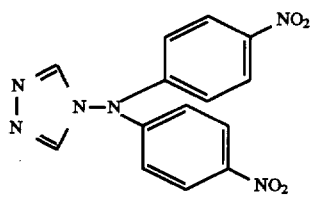

4-[Bis(4-nitrophenyl)amino]-4H-1,2,4-triazole

Starting Compounds: 4-[(4-nitrophenyl)amino]-4H-1,2,4-triazole and 4-fluoronitrobenzene Elementary Analysis (for $C_{14}H_{10}N_6O_4$)

|  | C (%) | H (%) | N (%) |
|---|---|---|---|
| Calculated: | 51.54 | 3.09 | 25.76 |
| Measured: | 51.59 | 3.14 | 25.80 |

Mass Spectrometry (m/z): 326 ($M^+$)

Nuclear Magnetic Resonance Spectrum (DMSO-$d_6$, TMS internal standard)

δ: 7.24 (4H, d, J=9 Hz), 8.30 (4H, d, J=9 Hz), 9.28 (2H, s)

EXAMPLE 9

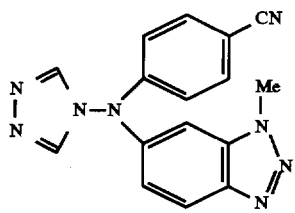

(i) The same process as in Example 2 was repeated, except that 4-fluoro-2-methylaminonitrobenzene was used in place of 4-fluorobenzonitrile, to give 4-[N-(4-cyanophenyl)-N-[(3-methylamino-4-nitro)phenyl]amino]-4H-1,2,4-triazole.

Nuclear Magnetic Resonance Spectrum (CDCl$_3$, TMS internal standard)

δ: 3.16 (3H, s), 7.23 (2H, d, J=8 Hz), 7.75 (2H, d, J=9 Hz), 7.80 (2H, s), 8.13 (2H, d, J=9 Hz), 8.87 (2H, s)

Mass Spectrometry (m/z): 335 ($M^+$)

(ii) 30 Milliliters of methanol and 1 g of Raney nickel were added to 1.8 g of 4-[N-(4-cyanophenyl)-N-[(3-methylamino-4-nitro)phenyl]amino]-4H-1,2,4-triazole as obtained in the previous (i) and the mixture was subjected to catalytic reduction in a hydrogen atmosphere under normal pressure. After the Raney nickel was removed and the solvent was removed by distillation under reduced pressure, the intended 4-[[N-(4-amino- 3-methyl-amino)phenyl]-N-(4-cyanophenyl)amino]-4H-1,2,4-triazole was quantitatively obtained. This was dissolved in 30 ml of 6N hydrochloric acid, and 2 ml of an aqueous solution of 0.37 g of sodium nitrite was added dropwise to the reaction mixture at the temperature below 5° C. After addition, the reaction mixture was stirred at the temperature below 5° C. for 30 minutes and then made alkaline with an aqueous sodium hydroxide solution. This was extracted with ethyl acetate, the organic layer separated was washed with water and dried over anhydrous magnesium sulfate, and the solvent was removed by distillation under reduced pressure. The residue was purified by silica gel column chromatography, and crude crystals were obtained from the ethyl acetate/methanol (100/1) eluate. These crude crystals were recrystallized from ethyl acetate to give 0.17 g of 6-[N-(4-cyanophenyl)-N-(4H-1,2,4-triazol-4-yl)amino]-1-methyl-1H-benzotriazole.

Nuclear Magnetic Resonance Spectrum (CDCl$_3$+DMSO-$d_6$, TMS internal standard)

δ: 2.81 (3H, s), 6.75 (2H, d, J=9 Hz), 7.36 (1H, dd, J=9 Hz, J=2 Hz), 7.59 (1H, d, J=2 Hz), 7.63 (1H, d, J=9 Hz), 8.11 (2H, d, J=9 Hz), 8.73 (2H, s)

Mass Spectrometry (m/z): 316 ($M^+$), 220

EXAMPLE 10

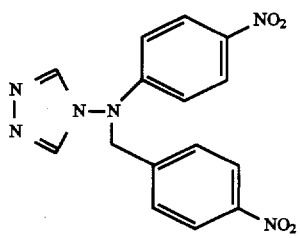

To a suspension of 0.37 g of 4-[(4-nitrophenyl)amino]-4H-1,2,4-triazole obtained in Referential Example 3 in 20 ml of 2-butanone were successively added 0.83 g of potassium carbonate anhydride, 1.30 g of p-nitrobenzyl bromide and a catalytic amount of sodium iodide, at room temperature, and the reaction mixture was then heated under reflux for about 2 hours. After cooled, the solvent was removed by distillation under reduced pressure, and a proper amount of water was added to the residue, which was then extracted several times each with ethyl acetate. The ethyl acetate layer separated was washed with water and dried over anhydrous magnesium sulfate, and the solvent was removed by distillation under reduced pressure. The residue formed was purified by silica gel column chromatography to give crude crystals from the chloroform/methanol (100/1) eluate. The crude crystals thus obtained were recrystallized from ethanol to give 0.28 g of 4-[N-(4-nitrobenzyl)-N-(4-nitrophenyl)amino]-4H-1,2,4-triazole.

Elementary Analysis (for $C_{15}H_{12}N_6O_4$)

|  | C (%) | H (%) | N (%) |
|---|---|---|---|
| Calculated: | 52.94 | 3.55 | 24.70 |
| Measured: | 52.94 | 3.62 | 25.02 |

Mass Spectrometry (m/z): 340 ($M^+$)

Nuclear Magnetic Resonance Spectrum (DMSO-$d_6$, TMS internal standard)

δ: 5.33 (2H, s), 6.77 (2H, d, J=9 Hz), 7.66 (2H, d, J=9 Hz), 8.20 (4H, d, J=9 Hz), 8.93 (2H, s)

EXAMPLE 11

In the same manner as in Example 10, the following compound was obtained.

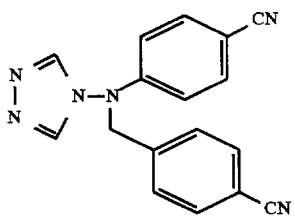

4-[N-(4-cyanobenzyl)-N-(4-cyanophenyl)amino]-4H-1,2,4-triazole

Starting Compounds: 4-[(4-cyanophenyl)amino-4H-1,2,4-triazole and 4-cyanobenzyl bromide Mass Spectrometry (m/z): 300 (M⁺)

Nuclear Magnetic Resonance Spectrum (CDCl₃, TMS internal standard)

δ: 4.98 (2H, s), 6.64 (2H, d, J=9 Hz), 7.26–7.74 (6H, m), 8.20 (2H, s)

EXAMPLE 12

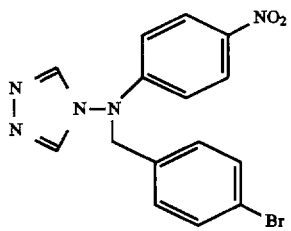

8 Milliliters of acetonitrile was added to 0.63 g of 4-[N-(4-nitrophenyl)amino]-4H-1,2,4-triazole, 0.82 g of 4-bromobenzyl bromide and 0.62 g of anhydrous potassium carbonate and the mixture was stirred for 3 hours at room temperature. The solvent was removed by distillation under reduced pressure, and water was added to the residue obtained, which was then extracted with chloroform. The chloroform layer separated was washed with water and dried over anhydrous magnesium sulfate, and the solvent was removed by distillation. The residue was purified by silica gel column chromatography to give crude crystals from the chloroform/methanol (100/1) eluate. The crude crystals were recrystallized from acetone to give 0.71 g of 4-[N-(4-bromobenzyl)-N-(4-nitrophenyl)amino]-4H-1,2,4-triazole.

Melting Point: 241° C.

Elementary Analysis (for $C_{15}H_{12}BrN_5O_2$)

|  | C (%) | H (%) | N (%) | Br (%) |
|---|---|---|---|---|
| Calculated: | 48.15 | 3.23 | 18.72 | 21.35 |
| Measured: | 48.21 | 3.17 | 18.97 | 21.50 |

Mass Spectrometry (m/z): 374 (M⁺) Nuclear Magnetic Resonance Spectrum (DMSO-d₆, TMS internal standard)

δ: 5.12 (2H, s), 6.79 (2H, d, J=9 Hz), 7.29 (2H, d, J=9 Hz), 7.54 (4H, d, J=9 Hz), 8.19 (2H, d, J=9 Hz), 8.84 (2H, s)

EXAMPLE 13

In the same manner as in Example 10, the following compound was obtained.

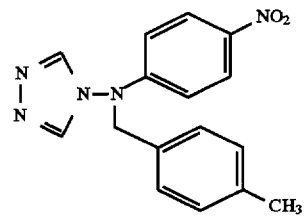

4-[N-(4-methylbenzyl)-N-(4-nitrophenyl)amino]-4H-1,2,4-triazole

Starting Compounds: 4-[(4-nitrophenyl)amino]-4H-1,2,4-triazole and 4-methylbenzyl bromide Elementary Analysis (for $C_{16}H_{15}N_5O_2$)

|  | C (%) | H (%) | N (%) |
|---|---|---|---|
| Calculated: | 62.13 | 4.89 | 22.64 |
| Measured: | 61.87 | 5.00 | 22.43 |

Mass Spectrometry (m/z): 309 (M⁺)

Nuclear Magnetic Resonance Spectrum (CDCl₃, TMS internal standard)

δ: 2.34 (3H, s), 4.90 (2H, s), 6.68 (2H, d, J=6 Hz), 7.08 (2H, d, J=8 Hz), 7.16 (2H, d, J=8 Hz), 8.10 (2H, s), 8.19 (2H, d, J=6 Hz)

EXAMPLE 14

In the same manner as in Example 10, the following compound was obtained.

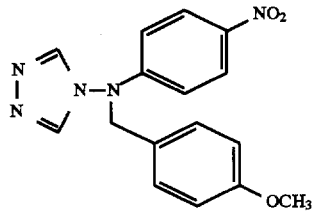

4-[N-(4-methoxybenzyl)-N-(4-nitrophenyl)amino]-4H-1,2,4-triazole

Starting Compounds: 4-[(4-nitrophenyl)amino]-4H-1,2,4-triazole and p-methoxybenzyl chloride Elementary Analysis (for $C_{16}H_{15}N_5O_3$)

|  | C (%) | H (%) | N (%) |
|---|---|---|---|
| Calculated: | 59.07 | 4.65 | 21.53 |
| Measured: | 59.05 | 4.61 | 21.50 |

Mass Spectrometry (m/z): 325 (M⁺)

Nuclear Magnetic Resonance Spectrum (DMSO-d₆, TMS internal standard)

δ: 3.73 (3H, s), 5.04 (2H, s), 6.76–6.92 (4H, m), 7.22 (2H, d, J=9 Hz), 8.19 (2H, d., J=9 Hz), 8.75 (2H, s)

EXAMPLE 15

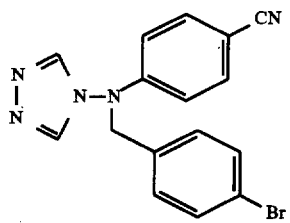

40 Milliliters of acetonitrile was added to 3.15 g of 4-[N-(4-cyanophenyl)amino]-4H-1,2,4-triazole, 4.25 g of 4-bromobenzyl bromide and 3.52 g of anhydride potassium carbonate and the mixture was stirred for 2 hours at room temperature. The solvent was removed by distillation under reduced pressure, and water was added to the residue formed, which was then extracted with chloroform. The chloroform layer separated was washed with water and dried over anhydrous magnesium sulfate, and the solvent was removed by distillation. The residue was purified by silica gel column chromatography to give crude crystals from the chloroform/methanol (100/1) eluate. The crude crystals were recrystallized from ethanol to give 3.92 g of 4-[N-(4-bromobenzyl)-N-(4-cyanophenyl)amino]-4H-1,2,4-triazole.

Melting Point: 203° C.

Elementary Analysis (for $C_{16}H_{12}BrN_5$)

|  | C (%) | H (%) | N (%) | Br (%) |
|---|---|---|---|---|
| Calculated: | 54.26 | 3.41 | 19.77 | 22.56 |
| Measured: | 53.96 | 3.48 | 19.72 | 22.65 |

Mass Spectrometry (m/z): 354 (M$^+$)

Nuclear Magnetic Resonance Spectrum (DMSO-$_6$, TMS internal standard)

δ: 5.06 (2H, s), 6.75 (2H, d, J=9 Hz), 7.27 (2H, d, J=9 Hz), 7.53 (2H, d, J=9 Hz), 7.75 (2H, d, J=9 Hz), 8.81 (2H, s)

EXAMPLE 16

In the same manner as in Example 10, the following compound was obtained.

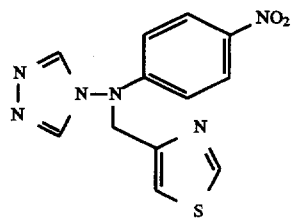

4-[N-(4-nitrophenyl)-N-(4-thiazolylmethyl)amino]-4H-1,2,4-triazole

Starting Compounds: 4-[(4-nitrophenyl)]amino-4H-1,2,4-triazole and 4-(chloromethyl)thiazole Elementary Analysis (for $C_{12}H_{10}N_6O_2S$)

|  | C (%) | H (%) | N (%) | S (%) |
|---|---|---|---|---|
| Calculated: | 47.68 | 3.33 | 27.80 | 10.61 |
| Measured: | 47.51 | 3.45 | 27.75 | 10.45 |

Mass Spectrometry (m/z): 302 (M$^+$)

Nuclear Magnetic Resonance Spectrum (DMSO-d$_6$, TMS internal standard)

δ: 5.28 (2H, s), 6.77 (2H, d, J=9 Hz), 7.77 (1H, brs), 8.17 (2H, d, J=9 Hz), 8.80 (2H, s), 9.12 (1H, brs)

EXAMPLE 17

In the same manner as in Example 10, the following compound was obtained.

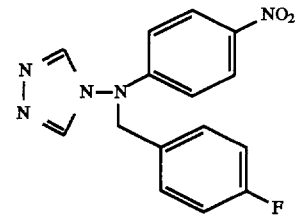

4-[N-(4-fluorobenzyl)-N-(4-nitrophenyl)amino]-4H-1,2,4-triazole

Starting Compounds: 4-[(4-nitrophenyl)]amino-4H-1,2,4-triazole and p-fluorobenzyl bromide Elementary Analysis (for $C_{15}H_{12}FN_5O_2$)

|  | C (%) | H (%) | N (%) | F (%) |
|---|---|---|---|---|
| Calculated: | 57.51 | 3.86 | 22.35 | 6.06 |
| Measured: | 57.44 | 3.98 | 22.37 | 5.85 |

Mass Spectrometry (m/z): 313 (M$^+$)

Nuclear Magnetic Resonance Spectrum (DMSO-$_6$, TMS internal standard)

δ: 5.12 (2H, s), 6.81 (2H, d, J=9 Hz), 7.05–7.46 (4H, m), 8.20 (2H, d, J=9 Hz), 8.81 (2H, s)

EXAMPLE 18

In the same manner as in Example 10, the following compound was obtained.

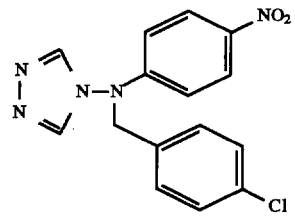

4-[N-(4-chlorobenzyl)-N-(4-nitrophenyl)amino]-4H-1,2,4-triazole

Starting Compounds: 4-[(4-nitrophenyl)amino]-4H-1,2,4-triazole and p-chlorobenzyl bromide Elementary Analysis (for $C_{15}H_{12}ClN_5O_2$)

|  | C (%) | H (%) | N (%) | Cl (%) |
|---|---|---|---|---|
| Calculated: | 54.64 | 3.67 | 21.24 | 10.75 |
| Measured: | 54.59 | 3.85 | 21.13 | 10.72 |

Mass Spectrometry (m/z): 329 (M$^+$)

Nuclear Magnetic Resonance Spectrum (DMSO-d$_6$, TMS internal standard)

δ: 5.14 (2H, s), 6.79 (2H, d, J=9 Hz), 7.36 (2H, d, J=9 Hz), 7.40 (2H, d, J=9 Hz), 8.20 (2H, d, J=9 Hz), 8.84 (2H, s)

EXAMPLE 19

In the same manner as in Example 10, the following compound was obtained.

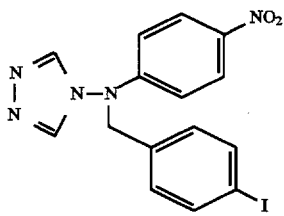

4-[N-(4-iodobenzyl)-N-(4-nitrophenyl)amino]-4H-1,2,4-triazole

Starting Compounds: 4-[(4-nitrophenyl)]amino-4H-1,2,4-triazole and p-iodobenzyl chloride Elementary Analysis (for $C_{15}H_{12}IN_3O_2$)

|  | C (%) | H (%) | N (%) | I (%) |
|---|---|---|---|---|
| Calculated: | 42.77 | 2.87 | 16.63 | 30.13 |
| Measured: | 42.68 | 3.01 | 16.46 | 30.26 |

Mass Spectrometry (m/z): 422 ($M^+ +1$)

Nuclear Magnetic Resonance Spectrum (DMSO-$d_6$, TMS internal standard)

δ: 5.10 (2H, s), 6.78 (2H, d, J=9 Hz), 7.14 (2H, d, J=9 Hz), 7.70 (2H, d, J=9 Hz), 8.19 (2H, d, J=9 Hz), 8.84 (2H, s)

EXAMPLE 20

In the same manner as in Example 10, the following compound was obtained.

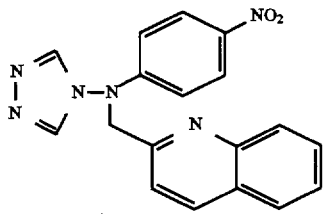

2-[[N-(4-nitrophenyl)-N-(4H-1,2,4-triazol-4-yl)amino]methyl]quinoline

Starting Compounds: 4-[(4-nitrophenyl)amino]-4H-1,2,4-triazole and 2-(chloromethyl)quinoline Elementary Analysis (for $C_{18}H_{14}N_6O_2$)

|  | C (%) | H (%) | N (%) |
|---|---|---|---|
| Calculated: | 62.42 | 4.07 | 24.26 |
| Measured: | 62.42 | 4.22 | 24.30 |

Mass Spectrometry (m/z): 347 ($M^+ +1$)

Nuclear Magnetic Resonance Spectrum (DMSO-$d_6$, TMS internal standard)

δ: 5.52 (2H, s), 6.70 (2H, d, J=8 Hz), 7.61 (1H, t, J=6 Hz), 7.67 (1H, d, J=7 Hz), 7.76 (1H, t, J=6 Hz), 7.98–8.03 (2H, m), 8.42 (1H, d, J=7 Hz), 9.08 (2H, s)

EXAMPLE 21

In the same manner as in Example 10, the following compound was obtained.

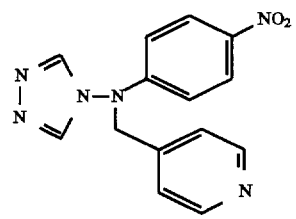

4-[N-(4-nitrophenyl)-N-(4-pyridylmethyl)amino]-4H-1,2,4-triazole

Starting Compounds: 4-[(4-nitrophenyl)amino]-4H-1,2,4-triazole and 4-picolyl chloride Elementary Analysis (for $C_{14}H_{12}N_6O_2$)

|  | C (%) | H (%) | N (%) |
|---|---|---|---|
| Calculated: | 56.75 | 4.08 | 28.36 |
| Measured: | 56.67 | 4.23 | 28.36 |

Mass Spectrometry (m/z): 297 ($M^+ +1$)

Nuclear Magnetic Resonance Spectrum (DMSO-d6, TMS internal standard)

δ: 5.23 (2H, s), 6.72 (2H, d, J=9 Hz), 7.40 (2H, d, J=6 Hz), 8.19 (2H, d, J=9 Hz), 8.55 (2H, d, J=6 Hz), 8.97 (2H, s)

EXAMPLE 22

In the same manner as in Example 10, the following compound was obtained.

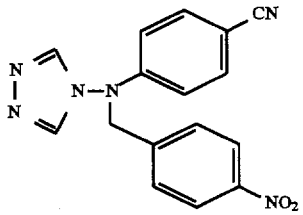

4-[N-(4-cyanophenyl)-N-(4-nitrophenyl)amino]-4H-1,2,4-triazole

Starting Compounds: 4-[(4-cyanophenyl)amino]-4H-1,2,4-triazole and 4-nitrobenzyl bromide Elementary Analysis (for $C_{16}H_{12}N_6O_2$)

|  | C (%) | H (%) | N (%) |
|---|---|---|---|
| Calculated: | 60.00 | 3.78 | 26.24 |
| Measured: | 59.75 | 3.71 | 26.28 |

Mass Spectrometry (m/z): 320 ($M^+$)

Nuclear Magnetic Resonance Spectrum (DMSO-$d_6$, TMS internal standard)

δ: 5.27 (2H, s), 6.74 (2H, d, J=9 Hz), 7.65 (2H, d, J=9 Hz), 7.77 (2H, d, J=9 Hz), 8.20 (2H, d, J=9 Hz), 8.90 (2H, s)

EXAMPLE 23

In the same manner as in Example 10, the following compound was obtained.

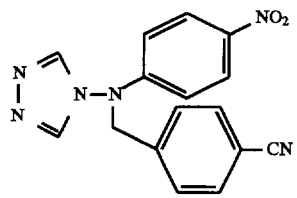

4-[N-(4-cyanobenzyl)-N-(4-nitrophenyl)amino]-4H-1,2,4-triazole

Starting Compounds: 4-[(4-nitrophenyl)amino]-4H-1,2,4-triazole and 4-cyanobenzyl bromide Elementary Analysis (for $C_{16}H_{12}N_6O_2$)

|  | C (%) | H (%) | N (%) |
|---|---|---|---|
| Calculated: | 60.00 | 3.78 | 26.24 |
| Measured: | 59.94 | 3.98 | 26.21 |

Mass Spectrometry (m/z): 320 (M$^+$, EI)

Nuclear Magnetic Resonance Spectrum (DMSO-$d_6$, TMS internal standard)

δ: 5.27 (2H, s), 6.76 (2H, d, J=9 Hz), 7.57 (2H, d, J=9 Hz), 7.84 (2H, d, J=9 Hz), 8.20 (2H, d, J=9 Hz), 8.91 (2H, s)

EXAMPLE 24

In the same manner as in Example 10, the following compound was obtained.

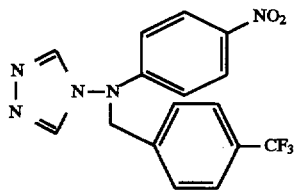

4-[N-(4-nitrophenyl)-N-[4-(trifluoromethyl)benzyl]-amino]-4H-1,2,4-triazole

Starting Compounds: 4-[(4-nitrophenyl)amino]-4H-1,2,4-triazole and 4-(trifluoromethyl)benzyl bromide Elementary Analysis (for $C_{16}H_{12}F_3N_5O_2$)

|  | C (%) | H (%) | N (%) | F (%) |
|---|---|---|---|---|
| Calculated: | 52.90 | 3.33 | 19.88 | 15.69 |
| Measured: | 52.88 | 3.36 | 19.38 | 15.60 |

Mass Spectrometry (m/z): 363 (M$^+$)

Nuclear Magnetic Resonance Spectrum (DMSO-$d_6$, TMS internal standard)

δ: 5.27 (2H, s), 6.78 (2H, d, J=7 Hz), 7.59 (2H, d, J=8 Hz), 7.72 (2H, d, J=8 Hz), 8.21 (2H, d, J=7 Hz), 8.91 (2H, s)

EXAMPLE 25

In the same manner as in Example 10, the following compound was obtained.

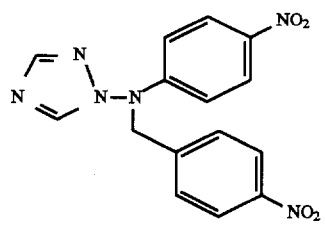

1-[N-(4-nitrobenzyl)-N-(4-nitrophenyl)amino]-1H-1,2,4-triazole

Starting Compounds: 1-[(4-nitrophenyl)amino]-1H-1,2,4-triazole and p-nitrobenzyl bromide Elementary Analysis (for $C_{15}H_{12}N_6O_4$)

|  | C (%) | H (%) | N (%) |
|---|---|---|---|
| Calculated: | 52.94 | 3.55 | 24.70 |
| Measured: | 52.66 | 3.74 | 24.62 |

Mass Spectrometry (m/z): 340 (M$^+$)

Nuclear Magnetic Resonance Spectrum (DMSO-$d_6$, TMS internal standard)

δ: 5.33 (2H, s), 6.75 (2H, d, J=9 Hz), 7.72 (2H, d, J=9 Hz), 8.10–8.27 (5H, m), 8.84 (1H, s)

EXAMPLE 26

In the same manner as in Example 10, the following compound was obtained.

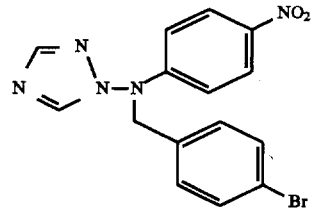

1-[N-(4-bromobenzyl)-N-(4-nitrophenyl)amino]-1H-1,2,4-triazole

Starting Compounds: 1-[(4-nitrophenyl)amino]-1H-1,2,4-triazole and p-bromobenzyl bromide Elementary Analysis (for $C_{15}H_{12}BrN_5O_2$)

|  | C (%) | H (%) | N (%) | Br (%) |
|---|---|---|---|---|
| Calculated: | 48.15 | 3.23 | 18.72 | 21.35 |
| Measured: | 48.00 | 3.31 | 18.72 | 21.42 |

Mass Spectrometry (m/z): 374 (M$^+$)

Nuclear Magnetic Resonance Spectrum (DMSO-$d_6$, TMS internal standard)

δ: 5.10 (2H, s), 6.76 (2H, d, J=9 Hz), 7.33 (2H, d, J=9 Hz), 7.54 (2H, d, J=9 Hz), 8.17 (2H, d, J=9 Hz), 8.20 (1H, s), 8.72 (1H, s)

EXAMPLE 27

In the same manner as in Example 10, the following compound was obtained.

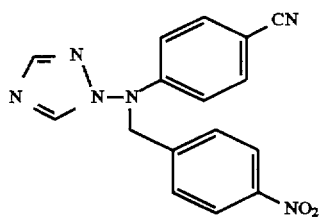

1-[N-(4-cyanophenyl)-N-(4-nitrobenzyl)amino]-1H-1,2,4-triazole

Starting Compounds: 1-[(4-cyanophenyl)amino]-1H-1,2,4-triazole and p-nitrobenzyl bromide Elementary Analysis (for $C_{16}H_{12}N_6O_2$)

|  | C (%) | H (%) | N (%) |
|---|---|---|---|
| Calculated: | 60.00 | 3.78 | 26.24 |
| Measured: | 60.02 | 3.91 | 26.21 |

Mass Spectrometry (m/z): 320 ($M^+$)

Nuclear Magnetic Resonance Spectrum ($CDCl_3$, TMS internal standard)

δ: 5.04 (2H, s), 6.67 (2H, d, J=9 Hz), 7.54 (2H, d, J=9 Hz), 7.58 (2Hi d, J=9 Hz), 7.96 (1H, s), 8.05 (1H, s), 8.21 (2H, d, J=9 Hz)

EXAMPLE 28

In the same manner as in Example 2, the following compound was obtained.

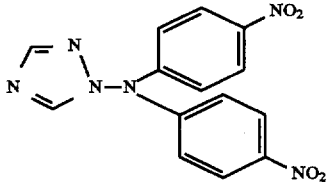

1-[Bis-(4-nitrophenyl)amino]-1H-1,2,4-triazole

Starting Compounds: 1-[(4-nitrophenyl)amino]-1H-1,2,4-triazole and p-nitrofluorobenzene Elementary Analysis (for $C_{14}H_{10}N_6O_4$)

|  | C (%) | H (%) | N (%) |
|---|---|---|---|
| Calculated: | 51.54 | 3.09 | 25.76 |
| Measured: | 51.39 | 3.43 | 25.36 |

Mass Spectrometry (m/z): 326 ($M^+$)

Nuclear Magnetic Resonance Spectrum (DMSO-$d_6$, TMS internal standard)

δ: 7.22 (4H, d, J=9 Hz), 8.28 (4H, d, J=9 Hz), 8.37 (1H, s), 9.24 (1H, s)

REFERENTIAL EXAMPLE 6

2.8 Milliliters of acetic anhydride was added to 15 ml of a pyridine solution containing 0.62 g of 4-[(4-nitrophenyl)amino]-4H-1,2,4-triazole at room temperature and the mixture was stirred for about 2 hours. After completion of reaction, the solvent was removed by distillation under reduced pressure, and a proper amount of an aqueous sodium hydrogencarbonate solution was added to the residue obtained, which was then extracted several times each with ethyl acetate. The ethyl acetate layer was washed with water and dried over anhydrous magnesium sulfate, and the solvent was removed by distillation under reduced pressure. The residue was purified by silica gel column chromatography to give 0.52 g of 4-[N-acetyl-N-(4-nitrophenyl)amino]-4H-1,2,4-triazole from the chloroform/methanol (100/1) eluate.

Mass Spectrometry (m/z): 247 ($M^+$)

Nuclear Magnetic Resonance Spectrum ($CDCl_3$, TMS internal standard)

δ: 2.13 (3H, s), 7.49 (2H, d, J=9 Hz), 8.28 (2H, d, J=9 Hz), 8.52 (2H, s)

REFERENTIAL EXAMPLE 7

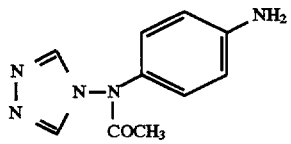

A proper amount of 10% palladium-carbon was added to 15 ml of a methanol solution containing 0.38 g of 4-[N-acetyl-N-(4-nitrophenyl)amino]-4H-1,2,4-triazole and the mixture was subjected to catalytic reduction in the presence of hydrogen gas at room temperature for about 40 minutes. After completion of reaction, the catalyst was removed by filtration, and the resulting filtrate was concentrated under reduced pressure. The residue was purified by silica gel column chromatography to give 0.33 g of 4-[N-acetyl-N-(4-aminophenyl)amino]-4H-1,2,4-triazole from the chloroform/methanol (50/1) eluate.

Mass Spectrometry (m/z): 217 ($M^+$)

Nuclear Magnetic Resonance Spectrum (DMSO-$d_6$, TMS internal standard)

δ: 1.97 (3H, s), 5.53 (2H, br), 6.58 (2H, d, J=9 Hz), 7.35 (2H, d, J=9 Hz), 8.88 (2H, s)

REFERENTIAL EXAMPLE 8

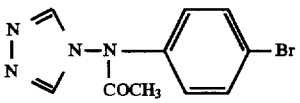

One Milliliter of a 47% hydrobromic acid solution containing 0.32 g of 4-[N-acetyl-N-(4-aminophenyl)amino]-

4H-1,2,4-triazole was cooled to 0 to 5° C., and 1 ml of an aqueous solution containing 0.1 g of sodium nitrite was gradually dropwise added thereto. The mixture was stirred for about 20 minutes at the same temperature. Subsequently, this was poured into a previously prepared cold aqueous solution containing 0.55 g of cuprous bromide and 1 ml of 47% hydrobromic acid and the mixture was stirred for about 20 hours at room temperature. The reaction mixture was neutralized with an aqueous sodium hydrogencarbonate solution and then extracted several times each with ethyl acetate. The ethyl acetate layer obtained was washed with water and dried over anhydrous magnesium sulfate. The solvent was removed by distillation under reduced pressure to give crude crystals, which were washed with ether to give 0.29 g of 4-[N-acetyl-N-(bromophenyl)amino)]-4H-1,2,4-triazole.

Mass Spectrometry (m/z): 281 (M⁺)

Nuclear Magnetic Resonance Spectrum (DMSO-d$_6$, TMS internal standard)

δ: 2.00 (3H, s), 7.74 (4H, m), 9.06 (2H, s)

REFERENTIAL EXAMPLE 9

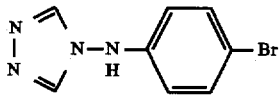

5 Milliliters of 4N hydrochloric acid was added to 0.22 g of 4-[N-acetyl-N-(4-bromophenyl)amino]-4H-1,2,4-triazole and the mixture was heated at 90° C. for about 40 minutes. After cooled, the solution was neutralized with an aqueous sodium hydrogen carbonate solution and then extracted several times each with ethyl acetate. The ethyl acetate layer obtained was washed with water and dried over anhydrous magnesium sulfate, and the solvent was removed by distillation under reduced pressure. The resulting residue was purified by silica gel column chromatography to give 0.18 g of 4-(4-bromophenyl)amino)-4H-1,2,4-triazole from the chloroform/methanol (50/1) eluate.

Mass Spectrometry (m/z): 239 (M⁺)

Nuclear Magnetic Resonance Spectrum (DMSO-d$_6$, TMS internal standard)

δ: 6.45 (2H, d, J=9 Hz), 7.41 (2H, d, J=9 Hz), 8.77 (2H, s), 9.62 (1H, s)

REFERENTIAL EXAMPLE 10

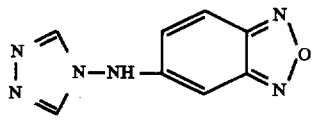

26.70 Grams of potassium tert-butoxide was dissolved in 100 ml of anhydrous dimethylsulfoxide and 20.00 g of 4-amino-4H-1,2,4-triazole was added thereto, followed by stirring for 2 hours at room temperature. Next, 50 ml of an anhydrous dimethylsulfoxide solution containing 11.00 g of 5-fluorobenzofurazane was added dropwise to the solution over a period of 20 minutes and then the mixture was stirred for 15 minutes. The reaction mixture was poured into 500 ml of water and 500 g of ice and then washed with 200 ml of ethyl acetate. The solution was then adjusted to have pH of 7.0 with 1N hydrochloric acid to give crystals. The crystals were collected by filtration, and the remaining mother liquid was extracted with ethyl acetate. The organic layer was washed with water and a saturated aqueous sodium chloride solution and then dried over anhydrous sodium sulfate. The solvent was removed by distillation under reduced pressure, and the crude crystals thus obtained were recrystallized from ethanol. These were combined with the previously obtained crystals to give 12.49 g of 5-[(4H-1,2,4-triazol-4-yl)amino] benzofurazane.

Mass Spectrometry (m/z): 202 (M⁺)

Nuclear Magnetic Resonance Spectrum (DMSO-d$_6$, TMS internal standard)

δ: 6.09 (1H, dd, J=2 Hz, 1 Hz), 7.29 (1H, dd, J=10 Hz, 2 Hz), 8.17 (1H, dd, J=10 Hz, 1 Hz), 8.89 (2H, s), 10.46 (1H, brs)

REFERENTIAL EXAMPLE 11

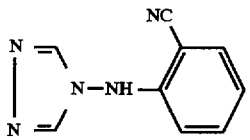

6.67 Grams of potassium tert-butoxide was dissolved in 36 ml of anhydrous dimethylsulfoxide, and 5.00 g of 4-amino-4H-1,2,4-triazole was added thereto and the mixture was stirred for 15 minutes at room temperature. Subsequently, 9 ml of an anhydrous dimethylsulfoxide solution containing 3.23 g of 2-fluorobenzonitrile was added dropwise to the solution over a period of 10 minutes, and the mixture was stirred for further 15 minutes. The reaction mixture was poured into 90 ml of water and 90 g of ice, and the solution was then adjusted to have pH of 5.7 with 1N hydrochloric acid. The crystals precipitated out were collected by filtration and dried to give 2.64 g of 4-[(2-cyanophenyl)amino]-4H-1,2,4-triazole.

Mass Spectrometry (m/z): 185 (M⁺)

Nuclear Magnetic Resonance Spectrum (DMSO-d$_6$, TMS internal standard)

δ: 6.22 (1H, d, J=8 Hz), 7.05 (1H, m), 7.54 (1H, m), 7.74 (1H, dd, J=8 Hz, 1 Hz), 8.81 (2H, s), 10.14 (1H, s)

EXAMPLE 29

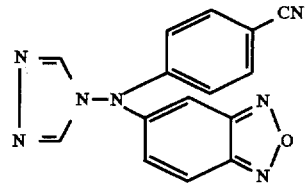

0.56 Gram of 4-[(4-cyanophenyl)amino]-4H-1,2,4-triazole was added little by little to a suspension of 0.12 g of sodium hydride in 6 ml of N,N-dimethylformamide at room temperature. After completion of the addition, the reaction mixture was stirred for 30 minutes at 50° C. and then cooled. With cooling, 0.42 g of 5-fluorobenzofrazane was added thereto and then the mixture was stirred for one hour at 100° C. The solvent was removed by distillation under reduced pressure, and water was added to the resulting residue, which was then extracted with chloroform. The chloroform layer was washed with water and dried over anhydrous magnesium sulfate, and the solvent was removed by distillation. The residue was purified by silica gel column chromatography to give crude crystals from the chloroform/methanol (200/1) eluate. The crude crystals were recrystallized from ethyl acetate to give 0.17 g of 5-[N-(4-cyanophenyl)-N-(4H-1,2,4-triazol-4-yl)amino] benzofrazane.

Elementary Analysis (for $C_{15}H_9N_7O$)

|  | C (%) | H (%) | N (%) |
|---|---|---|---|
| Calculated: | 59.40 | 2.99 | 32.33 |
| Measured: | 59.43 | 3.01 | 32.38 |

Nuclear Magnetic Resonance Spectrum ($CDCl_3$, TMS internal standard)

δ: 7.06–7.27 (4H, m), 7.74 (2H, d, J=9 Hz), 7.93 (1H, d, J=9 Hz), 8.49 (2H, s)

EXAMPLE 30

In the same manner as in Example 29, the following compound was obtained.

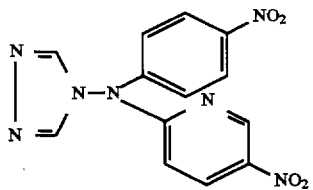

4-[N-(4-nitrophenyl)-N-(5-nitropyridin-2-yl)amino]-4H-1,2,4-triazole

Starting Compounds: 4-[(4-nitrophenyl)amino]-4H-1,2,4-triazole and 2-bromo-5-nitropyridine Elementary Analysis (for $C_{13}H_9N_7O_4$)

|  | C (%) | H (%) | N (%) |
|---|---|---|---|
| Calculated: | 47.71 | 2.77 | 29.96 |
| Measured: | 47.46 | 2.90 | 30.04 |

Mass Spectrometry (m/z): 327 ($M^+$)

Nuclear Magnetic Resonance Spectrum (DMSO-$d_6$, TMS internal standard)

δ: 6.77 (1H, d, J=9 Hz), 7.74 (2H, d, J=9 Hz), 8.38 (2H, d, J=9 Hz), 8.53 (1H, d, J=9 Hz), 9.13 (1H, s), 9.25 (2H, s)

EXAMPLE 31

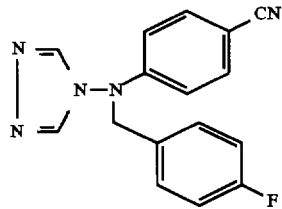

40 Milliliters of acetonitrile was added to 500 mg of 4-[(4-cyanophenyl)amino]-4H-1,2,4-triazole, 0.42 ml of 4-fluorobenzyl bromide and 746 mg of potassium carbonate and the mixture was stirred for 2 hours at room temperature. The solvent was removed by distillation under reduced pressure, and water was added to the resulting residue, which was then extracted with chloroform. The chloroform layer was dried over anhydrous magnesium sulfate and the solvent was removed by distillation. The residue was subjected to silica gel column chromatography to give crude crystals from the chloroform/methanol (100/2) eluate. The crude crystals were recrystallized from ethyl acetate to give 314 mg of 4-[N-(4-cyanophenyl)-N-(4-fluorobenzyl)amino]-4H-1,2,4-triazole.

Elementary Analysis (for $C_{16}H_{12}N_5F$)

|  | C (%) | H (%) | N (%) | F (%) |
|---|---|---|---|---|
| Calculated: | 65.52 | 4.12 | 23.88 | 6.48 |
| Measured: | 65.53 | 4.16 | 23.93 | 6.43 |

Mass Spectrometry (m/z): 293 ($M^+$)

Nuclear Magnetic Resonance Spectrum (DMSO-$d_6$, TMS internal standard)

δ: 5.05 (2H, s), 6.77 (2H, d, J=9 Hz), 7.04–7.44 (4H, m), 7.76 (2H, d, J=9 Hz), 8.78 (2H, s)

EXAMPLE 32

In the same manner as in Example 31, the following compound was obtained.

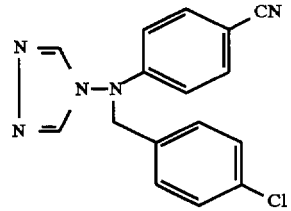

4-[N-(4-chlorobenzyl)-N-(4-cyanophenyl)amino]-4H-1,2,4-triazole

Starting Compounds: 4-[(4-cyanophenyl)amino]-4H-1,2,4-triazole and 4-chlorobenzyl bromide Elementary Analysis (for $C_{16}H_{12}N_5Cl$)

|  | C (%) | H (%) | N (%) | Cl (%) |
|---|---|---|---|---|
| Calculated: | 62.04 | 3.90 | 22.61 | 11.45 |
| Measured: | 61.97 | 4.10 | 22.59 | 11.26 |

Mass Spectrometry (m/z): 309 ($M^+$)

Nuclear Magnetic Resonance Spectrum (DMSO-$d_6$, TMS internal standard)

δ: 5.07 (2H, s), 6.75 (2H, d, J=9 Hz), 7.37 (4H, s), 7.76 (2H, d, J=9 Hz), 8.80 (2H, s)

EXAMPLE 33

In the same manner as in Example 31, the following compound was obtained.

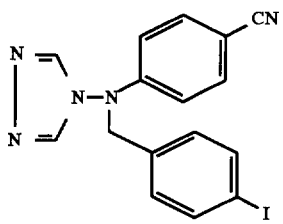

4-[N-(4-cyanophenyl)-N-(4-iodobenzyl)amino]-4H-1,2,4-triazole

Starting Compounds: 4-[(4-cyanophenyl)amino]-4H-1,2,4-triazole and 4-iodobenzyl chloride Elementary Analysis (for $C_6H_{12}N_5I$)

|  | C (%) | H (%) | N (%) | I (%) |
|---|---|---|---|---|
| Calculated: | 47.90 | 3.01 | 17.46 | 31.63 |
| Measured: | 47.76 | 3.05 | 17.46 | 31.51 |

Mass Spectrometry (m/z): 401 ($M^+$)

Nuclear Magnetic Resonance Spectrum (DMSO-$d_6$, TMS internal standard)

δ: 5.03 (2H, s), 6.74 (2H, d, J=9 Hz), 7.13 (2H, d, J=8 Hz), 7.68 (2H, d, J=8 Hz), 7.76 (2H, d, J=9 Hz), 8.81 (2H, s)

EXAMPLE 34

In the same manner as in Example 31, the following compound was obtained.

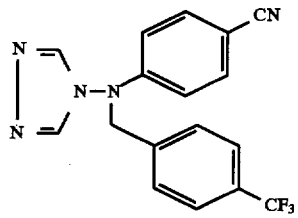

4-[N-(4-cyanophenyl)-N-[(4-trifluoromethyl)benzyl]amino]-4H-1,2,4-triazole

Starting Compounds: 4-[(4-cyanophenyl)amino]-4H-1,2,4-triazole and 4-(trifluoromethyl)benzyl bromide Elementary Analysis (for $C_{17}H_{12}N_5F_3$)

|  | C (%) | H (%) | N (%) | F (%) |
|---|---|---|---|---|
| Calculated: | 59.48 | 3.52 | 20.40 | 16.60 |
| Measured: | 59.40 | 3.59 | 20.41 | 16.48 |

Mass Spectrometry (m/z): 343 ($M^+$)

Nuclear Magnetic Resonance Spectrum (DMSO-$d_6$, TMS internal standard)

δ: 5.20 (2H, s), 6.75 (2H, d, J=9 Hz), 7.58 (2H, d, J=8 Hz), 7.71 (2H, d, J=8 Hz), 7.77 (2H, d, J=9 Hz), 8.88 (2H, s)

EXAMPLE 35

In the same manner as in Example 31, the following compound was obtained.

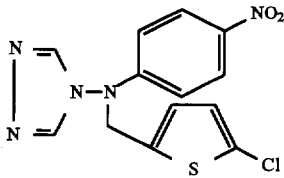

4-[N-[(5-chlorothiophen-2-yl)methyl]-N-(4-nitrophenyl)amino]-4H-1,2,4-triazole

Starting Compounds: 4-[(4-nitrophenyl)amino]-4H-1,2,4-triazole and 2-chloro-5-(chloromethyl)-thiophene Elementary Analysis (for $C_{13}H_{10}N_5ClO_2S$)

|  | C (%) | H (%) | N (%) | Cl (%) | S (%) |
|---|---|---|---|---|---|
| Calculated: | 46.50 | 3.00 | 20.86 | 10.56 | 9.55 |
| Measured: | 46.30 | 3.02 | 20.78 | 10.69 | 9.48 |

Mass Spectrometry (m/z): 335 ($M^+$)

Nuclear Magnetic Resonance Spectrum (DMSO-$d_6$, TMS internal standard)

δ: 5.30 (2H, s), 6.74–7.02 (4H, m), 8.20 (2H, d, J=10 Hz), 8.81 (2H, s)

EXAMPLE 36

In the same manner as in Example 31, the following compound was obtained.

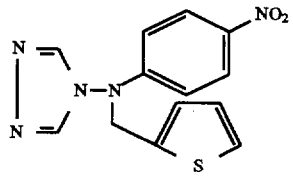

4-[N-(4-nitrophenyl)-N-(thienylmethyl)amino]-4H-1,2,4-triazole

Starting Compounds: 4-[(4-nitrophenyl)amino]-4H-1,2,4-triazole and 2-(chloromethyl)thiophene Elementary Analysis (for $C_{13}H_{11}N_5O_2S$)

|  | C (%) | H (%) | N (%) | S (%) |
|---|---|---|---|---|
| Calculated: | 51.82 | 3.68 | 23.24 | 10.64 |
| Measured: | 51.94 | 3.72 | 23.10 | 10.60 |

Mass Spectrometry (m/z): 301 ($M^+$)

Nuclear Magnetic Resonance Spectrum (DMSO-$d_6$, TMS internal standard)

δ: 5.35 (2H, s), 6.80–7.02 (4H, m), 7.54 (1H, d, J=5 Hz), 8.20 (2H, d, J=10 Hz), 8.74 (2H, s)

EXAMPLE 37

In the same manner as in Example 31, the following compound was obtained.

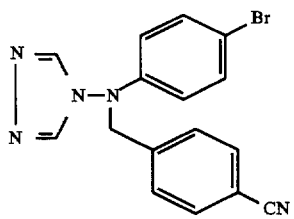

4-[N-(4-bromophenyl)-N-(4-cyanobenzyl)amino]-4H-1,2,4-triazole

Starting Compounds: 4-[(4-bromophenyl)amino]-4H-1,2,4-triazole and α-bromo-p-tolunitrile Elementary Analysis (for $C_{16}H_{12}N_5Br$)

|  | C (%) | H (%) | N (%) | Br (%) |
|---|---|---|---|---|
| Calculated: | 54.26 | 3.41 | 19.77 | 22.56 |
| Measured: | 54.17 | 3.55 | 19.70 | 22.43 |

Mass Spectrometry (m/z): 354 (M$^+$)

Nuclear Magnetic Resonance Spectrum (DMSO-d$_6$, TMS internal standard)

δ: 5.07 (2H, s), 6.66 (2H, d, J=10 Hz), 7.45–7.90 (6H, m), 8.84 (2H, s)

EXAMPLE 38

In the same manner as in Example 31, the following compound was obtained.

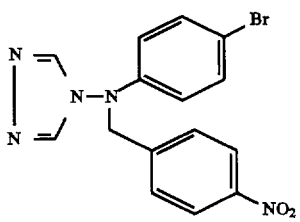

4-[N-(4-bromophenyl)-N-(4-nitrobenzyl)amino]-4H-1,2,4-triazole

Starting Compounds: 4-[(4-bromophenyl)amino]-4H-1,2,4-triazole and 4-nitrobenzyl bromide Elementary Analysis (for $C_{15}H_{12}N_5O_2Br$)

|  | C (%) | H (%) | N (%) | Br (%) |
|---|---|---|---|---|
| Calculated: | 48.15 | 3.23 | 18.72 | 21.35 |
| Measured: | 48.08 | 3.39 | 18.66 | 21.19 |

Mass Spectrometry (m/z): 374 (M$^+$)

Nuclear Magnetic Resonance Spectrum (DMSO-d$_6$, TMS internal standard)

δ: 5.13 (2H, s), 6.68 (2H, d, J=9 Hz), 7.51 (2H, d, J=9 Hz), 7.65 (2H, d, J=9 Hz), 8.19 (2H, d, J=9 Hz), 8.88 (2H, s)

EXAMPLE 39

In the same manner as in Example 31, the following compound was obtained.

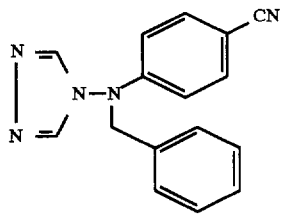

4-[N-benzyl-N-(4-cyanophenyl)amino]-4H-1,2,4-triazole

Starting Compounds: 4-[(4-cyanophenyl)amino]-4H-1,2,4-triazole and benzyl bromide Elementary Analysis (for $C_{16}H_{13}N_5$)

|  | C (%) | H (%) | N (%) |
|---|---|---|---|
| Calculated: | 69.80 | 4.76 | 25.44 |
| Measured: | 69.66 | 4.84 | 25.43 |

Mass Spectrometry (m/z): 275 (M$^+$)

Nuclear Magnetic Resonance Spectrum (DMSO-$_6$, TMS internal standard)

δ: 5.07 (2H, s), 6.76 (2H, d, J=9 Hz), 7.32 (5H, s), 7.76 (2H, d, J=9 Hz), 8.80 (2H, s)

EXAMPLE 40

In the same manner as in Example 31, the following compound was obtained.

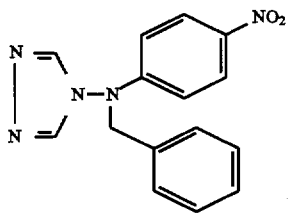

4-[N-benzyl-N-(4-nitrophenyl)amino]-4H-1,2,4-triazole

Starting Compounds: 4-[(4-nitrobenzyl)amino]-4H-1,2,4-triazole and benzyl bromide Elementary Analysis (for $C_{15}H_{13}N_5O_2$)

|  | C (%) | H (%) | N (%) |
|---|---|---|---|
| Calculated: | 61.01 | 4.44 | 23.72 |
| Measured: | 60.68 | 4.49 | 25.67 |

Mass Spectrometry (m/z): 295 (M$^+$)

Nuclear Magnetic Resonance Spectrum (DMSO-d6, TMS internal standard)

δ: 5.13 (2H, s), 6.79 (2H, d, J=9 Hz), 7.33 (5H, s), 8.20 (2H, d, J=9 Hz), 8.83 (2H, s)

EXAMPLE 41

In the same manner as in Example 31, the following compound was obtained.

37

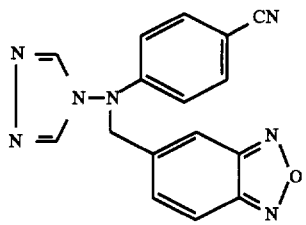

5-[[N-(4-cyanophenyl)-N-(4H-1,2,4-triazol-4-yl)amino]methyl]benzofurazan

Starting Compounds: 4-[(4-cyanophenyl)amino]-4H-1,2,4-triazole and 5-bromomethylbenzofurazan Elementary Analysis (for $C_{16}H_{11}N_7O$)

|  | C (%) | H (%) | N (%) |
|---|---|---|---|
| Calculated: | 60.56 | 3.49 | 30.90 |
| Measured: | 60.56 | 3.41 | 31.05 |

Mass Spectrometry (m/z): 317 ($M^+$)

Nuclear Magnetic Resonance Spectrum (DMSO-$d_6$, TMS internal standard)

δ: 5.27 (2H, s), 6.75 (2H, d, J=9 Hz), 7.61 (1H, d, J=9 Hz), 7.78 (2H, d, J=9 Hz), 8.02 (1H, s), 8.08 (1H, d, J=9 Hz), 8.99 (2H, s)

EXAMPLE 42

In the same manner as in Example 31, the following compound was obtained.

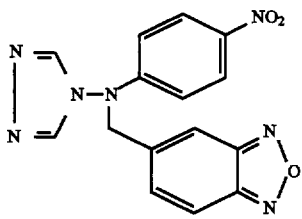

5-[[N-(4-nitrophenyl)-N-(4H-1,2,4-triazol-4-yl)amino]methyl]benzofurazan

Starting Compounds: 4-[(4-nitrophenyl)amino]-4H-1,2,4-triazole and 5-bromomethylbenzofurazan Elementary Analysis (for $C_{15}H_{11}N_7O_3$)

|  | C (%) | H (%) | N (%) |
|---|---|---|---|
| Calculated: | 53.41 | 3.29 | 29.07 |
| Measured: | 53.27 | 3.38 | 29.08 |

Mass Spectrometry (m/z): 337 ($M^+$)

Nuclear Magnetic Resonance Spectrum (DMSO-$d_6$, TMS internal standard)

δ: 5.33 (2H, s), 6.78 (2H, d, J=7 Hz), 7.61 (1H, d, J=9 Hz), 8.04 (1H, s), 8.09 (1H, d, J=9 Hz), 8.21 (2H, d, J=7 Hz), 9.03 (2H, s)

EXAMPLE 43

In the same manner as in Example 31, the following compound was obtained.

38

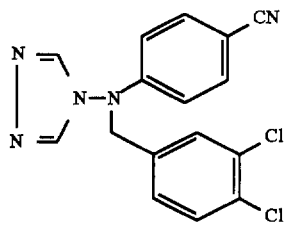

4-[N-(4-cyanophenyl)-N-(3,4-dichlorobenzyl)amino]-4H-1,2,4-triazole

Starting Compounds: 4-[(4-cyanophenyl)amino]-4H-1,2,4-triazole and 3,4-dichlorobenzyl chloride Elementary Analysis (for $C_{16}H_{11}Cl_2N_5$)

|  | C (%) | H (%) | N (%) | Cl (%) |
|---|---|---|---|---|
| Calculated: | 55.83 | 3.22 | 20.35 | 20.60 |
| Measured: | 55.98 | 3.27 | 20.48 | 20.46 |

Nuclear Magnetic Resonance Spectrum (DMSO-$d_6$, TMS internal standard)

δ: 5.09 (2H, s), 6.74 (2H, d, J=9 Hz), 7.31 (2H, dd, J=9 Hz, J=2 Hz), 7.60 (1H, d, J=9 Hz), 7.63 (1H, d, J=2 Hz), 7.77 (2H, d, J=9 Hz), 8.86 (2H, s)

EXAMPLE 44

In the same manner as in Example 31, the following compound was obtained.

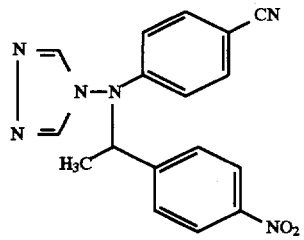

4-[N-(4-cyanophenyl)-N-[1-(4-nitrophenyl)ethyl]-amino]-4H-1,2,4-triazole

Starting Compounds: 4-[(4-cyanophenyl)amino]-4H-1,2,4-triazole and 4-(1-iodoethyl)nitrobenzene Elementary Analysis (for $C_{17}H_{14}N_6O_2$)

|  | C (%) | H (%) | N (%) |
|---|---|---|---|
| Calculated: | 61.07 | 4.22 | 25.14 |
| Measured: | 60.92 | 4.27 | 25.11 |

Mass Spectrometry (m/z): 334 ($M^+$)

Nuclear Magnetic Resonance Spectrum (DMSO-$d_6$, TMS internal standard)

δ: 1.48 (3H, d, J=7 Hz), 5.88 (1H, q, J=7 Hz), 6.66 (2H, d, J=9 Hz), 7.68 (2H, d, J=9 Hz), 7.74 (2H, d, J=9 Hz), 8.20 (2H, d, J=9 Hz), 8.77 (2H, s)

EXAMPLE 45

In the same manner as in Example 31, the following compound was obtained.

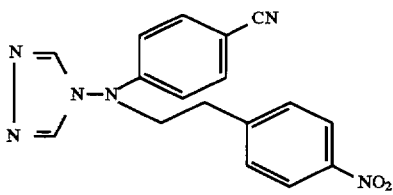

4-[[N-(4-cyanophenyl)-N-[2-(4-nitrophenyl)ethyl]-amino]-4H-1,2,4-triazole

Starting Compounds: 4-[(4-cyanophenyl)amino]-4H-1,2,4-triazole and 4-nitrophenethyl bromide Elementary Analysis (for $C_{17}H_{14}N_6O_2$)

|  | C (%) | H (%) | N (%) |
|---|---|---|---|
| Calculated: | 61.07 | 4.22 | 25.14 |
| Measured: | 61.01 | 4.26 | 25.14 |

Mass Spectrometry (m/z): 334 (M⁺)

Nuclear Magnetic Resonance Spectrum (DMSO-$d_6$, TMS internal standard)

δ: 2.99 (2H, t, J=7 Hz), 4.18 (2H, t, J=7 Hz), 6.26 (2H, d, J=9 Hz), 7.61 (2H, d, J=9 Hz), 7.72 (2H, d, J=9 Hz), 8.17 (2H, d, J=9 Hz), 8.88 (2H, s)

EXAMPLE 46

In the same manner as in Example 31, the following compound was obtained.

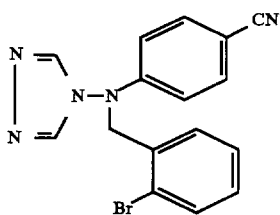

4-[N-(2-bromobenzyl)-N-(4-cyanophenyl)amino]-4H-1,2,4-triazole

Starting Compounds: 4-[(4-cyanophenyl)amino]-4H-1,2,4-triazole and 2-bromobenzyl bromide Elementary Analysis (for $C_6H_{12}BrN_5$)

|  | C (%) | H (%) | N (%) | Br (%) |
|---|---|---|---|---|
| Calculated: | 54.26 | 3.41 | 19.77 | 22.56 |
| Measured: | 54.10 | 3.32 | 19.85 | 22.72 |

Mass Spectrometry (m/z): 353 (M⁺)

Nuclear Magnetic Resonance Spectrum (DMSO-$d_6$, TMS internal standard)

δ: 5.14 (2H, s), 6.75 (2H, d, J=9 Hz), 7.27–7.36 (3H, m), 7.65 (1H, d, J=7 Hz), 7.78 (2H, d, J=9 Hz), 8.80 (2H, s)

EXAMPLE 47

In the same manner as in Example 31, the following compound was obtained.

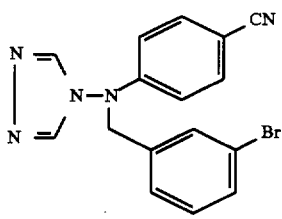

4-[N-(3-bromobenzyl)-N-(4-cyanophenyl)amino]-4H-1,2,4-triazole

Starting Compounds: 4-[(cyanophenyl)amino]-4H-1,2,4-triazole and 3-bromobenzyl bromide Elementary Analysis (for $C_{16}H_{12}BrN_5$)

|  | C (%) | H (%) | N (%) | Br (%) |
|---|---|---|---|---|
| Calculated: | 54.26 | 3.41 | 19.77 | 22.56 |
| Measured: | 54.16 | 3.29 | 19.89 | 22.59 |

Mass Spectrometry (m/z): 353 (M⁺)

Nuclear Magnetic Resonance Spectrum (DMSO-$d_6$, TMS internal standard)

δ: 5.09 (2H, s), 6.75 (2H, d, J=9 Hz), 7.27-7.34 (2H, m), 7.50 (1H, d, J=7 Hz), 7.56 (1H, s), 7.77 (2H, d, J=9 Hz), 8.86 (2H, s)

EXAMPLE 48

In the same manner as in Example 31, the following compound was obtained.

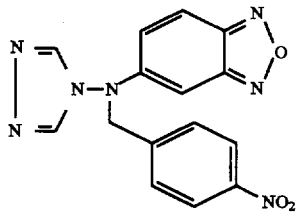

5-[N-(4-nitrobenzyl)-N-(4H-1,2,4-triazol-4-yl)amino]benzofurazan

Starting Compounds: 5-[(4H-1,2,4-triazol-4-yl)amino]benzofurazan and 4-nitrobenzyl bromide Elementary Analysis (for $C_{15}H_{11}N_7O_3$)

|  | C (%) | H (%) | N (%) |
|---|---|---|---|
| Calculated: | 53.41 | 3.29 | 29.07 |
| Measured: | 53.13 | 3.28 | 29.10 |

Mass Spectrometry (m/z): 337 (M⁺)

Nuclear Magnetic Resonance Spectrum (DMSO-$d_6$, TMS internal standard)

δ: 5.29 (2H, s), 7.04 (1H, dd, J=10 Hz, 2 Hz), 7.15 (1H, d, J=2 Hz), 7.69 (2H, d, J=9 Hz), 8.05 (1H, d, J=10 Hz), 8.21 (2H, d, J=9 Hz), 8.92 (2H, s)

EXAMPLE 49

In the same manner as in Example 31, the following compound was obtained.

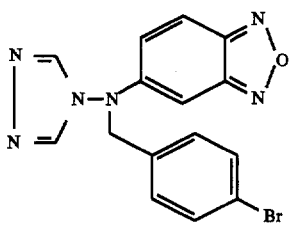

5-[N-(4-bromobenzyl)-N-(4H-1,2,4-triazol-4-yl)amino]benzofurazan

Starting Compounds: 5-[(4H-1,2,4-triazol-4-yl)amino]benzofurazan and 4-bromobenzyl bromide Elementary Analysis (for $C_{15}H_{11}BrN_6O$)

|  | C (%) | H (%) | N (%) | Br (%) |
|---|---|---|---|---|
| Calculated: | 48.54 | 2.99 | 22.64 | 21.53 |
| Measured: | 48.36 | 3.03 | 22.71 | 21.67 |

Mass Spectrometry (m/z): 370 ($M^+$)

Nuclear Magnetic Resonance Spectrum (DMSO-$d_6$, TMS internal standard)

δ: 5.07 (2H, s), 7.02 (1H, dd, J=10 Hz, 2 Hz), 7.18 (1H, d, J=2 Hz), 7.31 (2H, d, J=8 Hz), 7.54 (2H, d, J=8 Hz), 8.03 (1H, d, J=10 Hz), 8.83 (2H, s)

EXAMPLE 50

In the same manner as in Example 31, the following compound was obtained.

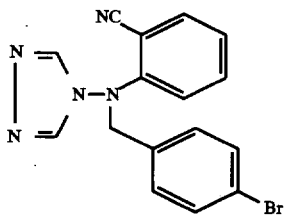

4-[N-(4-bromobenzyl)-N-(2-cyanophenyl)amino]-4H-1,2,4-triazole

Starting Compounds: 4-[(2-cyanophenyl)amino]-4H-1,2,4-triazole and 4-bromobenzyl bromide Elementary Analysis (for $C_{16}H_{12}N_5Br$)

|  | C (%) | H (%) | N (%) | Br (%) |
|---|---|---|---|---|
| Calculated: | 54.26 | 3.41 | 19.77 | 22.56 |
| Measured: | 54.19 | 3.41 | 19.90 | 22.42 |

Mass Spectrometry (m/z): 355 ($M^+$)

Nuclear Magnetic Resonance Spectrum (DMSO-$_6$, TMS internal standard)

δ: 4.92 (2H, s), 7.37 (2H, d, J=9 Hz), 7.40–7.53 (2H, m), 7.54 (2H, d, J=9 Hz ), 7.75–7.79 (1H, m), 7.89 (1H, d, J=8 Hz), 8.86 (2H, s)

EXAMPLE 51

In the same manner as in Example 31, the following compound was obtained.

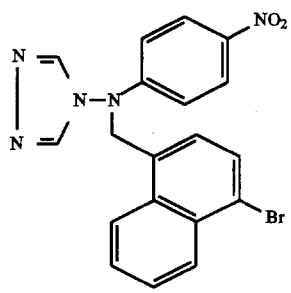

4-[[N-(4-bromonaphthalen-1-yl )methyl]-N-(4-nitrophenyl)amino]-4H-1,2,4-triazole Starting Compounds: 4-[(4-nitrophenyl)amino]-4H-1,2,4-triazole and α,4-dibromo-1-methylnaphthalene Elementary Analysis (for $C_{19}H_{14}N_5BrO_2$)

|  | C (%) | H (%) | N (%) | Br (%) |
|---|---|---|---|---|
| Calculated: | 53.79 | 3.33 | 16.51 | 18.83 |
| Measured: | 53.77 | 3.38 | 16.46 | 18.87 |

Mass Spectrometry (m/z): 42.5 ($M^+$)

Nuclear Magnetic Resonance Spectrum (DMSO-$d_6$, TMS internal standard)

δ: 5.61 (2H, s), 6.90 (2H, d, J=9 Hz), 7.35 (1H, d, J=8 Hz) 7.68–7.83 (3H, m), 8.09–8.29 (4H, m), 8.64 (2H, s)

EXAMPLE 52

In the same manner as in Example 31, the following compound was obtained.

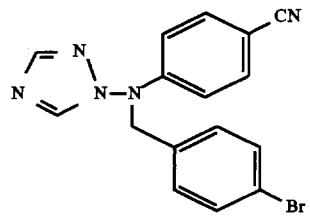

1-[N-(4-bromobenzyl)-N-(4-cyanophenyl)amino]-1H-1,2,4-triazole

Starting Compounds: 1-[(4-cyanophenyl)amino]-1H-1,2,4-triazole and 4-bromobenzyl bromide Physicochemical Properties:

Elementary Analysis (for $C_{16}H_{12}N_5Br$)

|  | C (%) | H (%) | N (%) | Br (%) |
|---|---|---|---|---|
| Calculated: | 54.26 | 3.41 | 19.77 | 22.56 |
| Measured: | 54.30 | 3.43 | 19.84 | 22.75 |

Mass Spectrometry (m/z): 353 ($M^+-1$)

Nuclear Magnetic Resonance Spectrum (CDCl$_3$, TMS internal standard)

δ: 4.87 (2H, s), 6.69 (2H, d, J=9 Hz), 7.14 (2H, d, J=9 Hz), 7.47 (2H, d, J=9 Hz), 7.57 (2H, d, J=9 Hz), 7.87 (1H, s), 8.03 (1H, s)

REFERENTIAL EXAMPLE 12

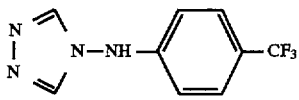

3.36 Grams of potassium tert-butoxide was added to 15 ml of anhydrous dimethylsulfoxide and the mixture was stirred for 30 minutes at room temperature. Next, 2.52 g of 4-amino-4H-1,2,4-triazole was added to the solution. After the reaction mixture was stirred for 15 minutes at room temperature, 1.64 g of 4-fluorobenzotrifluoride was added thereto and the mixture was stirred for further 30 minutes at room temperature. Ice-water was added to the reaction mixture, which was then neutralized with a diluted hydrochloric acid. The crystals as precipitated out were collected by filtration to give 1.93 g of 4-[(4-trifluoromethylphenyl)amino]-4H-1,2,4-triazole.

Nuclear Magnetic Resonance Spectrum (DMSO-$d_6$, TMS internal standard)

δ: 6.62 (2H, d, J=8 Hz), 7.60 (2H, d, J=8 Hz), 8.82 (2H, s), 10.06 (1H, br)

EXAMPLE 53

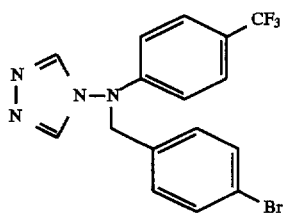

0.23 Gram of 4-[(4-trifluoromethylphenyl)-amino]-4H-1,2,4-triazole, 0.28 g of 4-bromobenzyl bromide and 0.17 g of anhydrous potassium carbonate were added to 5 ml of acetonitrile and the mixture was stirred for 3 hours at room temperature. The solvent was removed by distillation and water was added to the residue, which was then extracted with chloroform. The chloroform layer was washed with water and dried over anhydrous magnesium sulfate, and the solvent was removed by distillation under reduced pressure. The residue was purified by silica gel column chromatography to give crude crystals from the chloroform eluate. The crude crystals were recrystallized from a mixed solvent of ethyl acetate/ether to give 0.22 g of 4-[N-(4-bromobenzyl)-N-(4-trifluoromethylphenyl)amino]-4H-1,2,4-triazole.

Elementary Analysis (for $C_{16}H_{12}N_4BrF_3$)

|  | C (%) | H (%) | N (%) | Br (%) | F (%) |
|---|---|---|---|---|---|
| Calculated: | 48.38 | 3.05 | 14.11 | 20.12 | 14.35 |
| Measured: | 48.46 | 3.04 | 14.06 | 20.36 | 14.12 |

Nuclear Magnetic Resonance Spectrum (CDCl$_3$, TMS internal standard)

δ: 4.86 (2H, s), 6.74 (2H, d, J=9 Hz), 7.13 (2H, d, J=9 Hz), 7.49 (2H, d, J=9 Hz), 7.57 (2H, d, J=9 Hz), 8.22 (2H, s)

In the same manner as in Example 53, the following compounds were obtained.

EXAMPLE 54

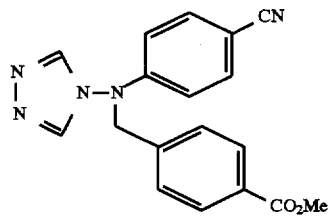

4-[N-(4-cyanophenyl)-N-(4-methoxycarbonylbenzyl)-amino]-4H-1,2,4-triazole

Starting Compounds: 4-[N-(4-cyanophenyl)amino]-4H-1,2,4-triazole and methyl 4-bromomethylbenzoate Elementary Analysis (for $C_{18}H_{15}N_5O_2$)

|  | C (%) | H (%) | N (%) |
|---|---|---|---|
| Calculated: | 64.86 | 4.54 | 21.01 |
| Measured: | 64.77 | 4.54 | 21.07 |

Mass Spectrometry (m/z): 333 (M⁺)

Nuclear Magnetic Resonance Spectrum (DMSO-$d_6$, TMS internal standard)

δ: 3.84 (3H, s), 5.18 (2H, s), 6.74 (2H, d, J=9 Hz), 7.49 (2H, d, J=9 Hz), 7.76 (2H, d, J=9 Hz), 7.91 (2H, d, J=9 Hz), 8.84 (2H, s)

EXAMPLE 55

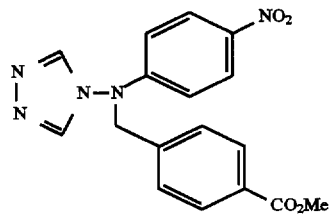

4-[N-(4-methoxycarbonylbenzyl)-N-(4-nitrophenyl)-amino]-4H-1,2,4-triazole

Starting Compounds: 4-[N-(4-nitrophenyl)amino]-4H-1,2,4-triazole and methyl 4-bromomethylbenzoate Elementary Analysis (for $C_{17}H_{15}N_5O_4$)

|  | C (%) | H (%) | N (%) |
|---|---|---|---|
| Calculated: | 57.79 | 4.28 | 19.82 |
| Measured: | 57.60 | 4.26 | 19.86 |

Mass Spectrometry (m/z): 353 (M⁺)

Nuclear Magnetic Resonance Spectrum (DMSO-$d_6$, TMS internal standard)

δ: 3.85 (3H, s), 5.25 (2H, s), 6.79 (2H, d, J=9 Hz), 7.51 (2H, d, J=8 Hz), 7.93 (2H, d, J=8 Hz), 8.20 (2H, d, J=9 Hz), 8.88 (2H, s)

EXAMPLE 56

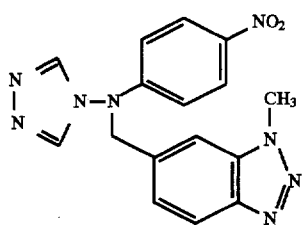

1-Methyl-6-[[N-(4-nitrophenyl)-N-(4H-1,2,4-triazol-4-yl) amino]methyl]-1H-benzotriazole Starting Compounds: 4-[(4-nitrophenyl)amino]-4H-1,2, 4-triazole and 6-chloromethyl-1-methyl-1H-benzotriazole Elementary Analysis (for $C_{16}H_{14}N_8O_2$)

|  | C (%) | H (%) | N (%) |
|---|---|---|---|
| Calculated: | 54.85 | 4.03 | 31.98 |
| Measured: | 54.83 | 4.05 | 32.21 |

Nuclear Magnetic Resonance Spectrum (DMSO-$d_6$, TMS internal standard)

δ: 4.28 (3H, s), 5.34 (2H, s), 6.82 (2H, d, J=9 Hz), 7.37 (2H, dd, J=9 Hz, 2 Hz), 7.84 (1H, d, J=2 Hz), 8.00 (2H, d, J=9 Hz), 8.21 (2H, d, J=9 Hz), 8.91 (2H, s)

EXAMPLE 57

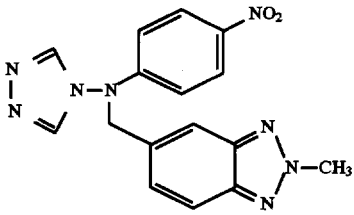

2-Methyl-5-[[N-(4-nitrophenyl)-N-(4H-1,2,4-triazol-4-yl) amino]methyl]-2H-benzotriazole Starting Compounds: 4-[(4-nitrophenyl)amino]-4H-1,2, 4-triazole and 5-chloromethyl-2-methyl-2H-benzotriazole Elementary Analysis (for $C_{16}H_{14}N_8O_2$)

|  | C (%) | H (%) | N (%) |
|---|---|---|---|
| Calculated: | 54.85 | 4.03 | 31.98 |
| Measured: | 54.68 | 4.02 | 32.08 |

Nuclear Magnetic Resonance Spectrum (DMSO-$d_6$, TMS internal standard)

δ: 4.74 (3H, s), 5.28 (2H, s), 6.84 (2H, d, J=9 Hz), 7.42 (2H, dd, J=9 Hz, 2 Hz), 7.84 (1H, d, J=2 Hz), 7.89 (2H, d, J=9 Hz), 8.21 (2H, d, J=9 Hz), 8.84 (2H, s)

EXAMPLE 58

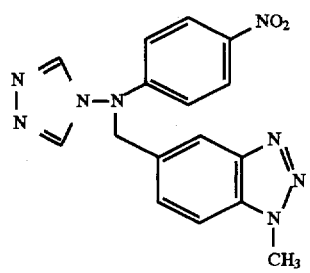

1-Methyl-5-[[N-(4-nitrophenyl)-N-(4H-1,2,4-triazol-4-yl) amino]methyl]-1H-benzotriazole Starting Compounds: 4-[(4-nitrophenyl)amino ]-4H-1,2. 4-triazole and 5-chloromethyl-1-methyl-1H-benzotriazole Elementary Analysis (for $C_{16}H_{14}N_8O_2$)

|  | C (%) | H (%) | N (%) |
|---|---|---|---|
| Calculated: | 54.85 | 4.03 | 31.98 |
| Measured: | 54.77 | 4.05 | 32.08 |

Nuclear Magnetic Resonance Spectrum (DMSO-$d_6$, TMS internal standard)

δ: 4.30 (3H, s), 5.30 (2H, s), 6.85 (2H, d, J=9 Hz), 7.54 (2H, dd, J=9 Hz, 2 Hz), 7.84 (2H, d, J=9 Hz), 7.98 (1H, d, J=2 Hz), 8.21 (2H, d, J=9 Hz), 8.84 (2H, s)

EXAMPLE 59

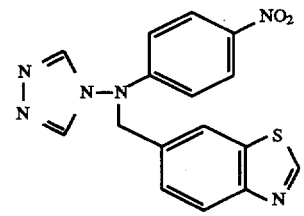

6-[[N-(4-nitrophenyl)-N-(4H-1,2,4-triazol-4-yl)amino] methyl]benzothiazole

Starting Compounds: 4-[(4-nitrophenyl)amino]-4H-1,2, 4-triazole and 6-(chloromethyl)benzothiazole Mass Spectrometry (m/z): 352 (M⁺)

Nuclear Magnetic Resonance Spectrum (DMSO-$d_6$, TMS internal standard)

δ: 5.31 (2H, s), 6.81 (2H, d, J=9 Hz), 7.52 (1H, dd, J=9 Hz, J=2 Hz), 8.06 (1H, d, J=9 Hz), 8.17 (1H, d, J=2 Hz), 8.21 (2H, d, J=9 Hz), 8.89 (2H, s), 9.40 (1H, s)

EXAMPLE 60

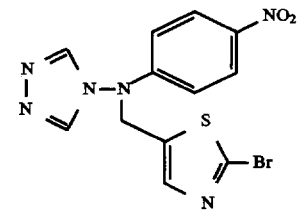

4-[N-[(2-bromothiazol-5-yl)methyl]-N-(4-nitrophenyl) amino]-4H-1,2,4-triazole

Starting Compounds: 4-(4-nitrophenyl)amino-4H-1,2,4-triazole and 2-bromo-5-(bromomethyl)thiazole Elementary Analysis (for $C_{12}H_7N_6O_2BrS$)

|  | C (%) | H (%) | N (%) | S (%) | Br (%) |
|---|---|---|---|---|---|
| Calculated: | 37.81 | 2.38 | 22.05 | 8.41 | 20.96 |
| Measured: | 37.64 | 2.35 | 21.96 | 8.29 | 20.71 |

Mass Spectrometry (m/z): 379 ($M^+$)

Nuclear Magnetic Resonance Spectrum (DMSO-$d_6$, TMS internal standard)

δ: 5.42 (2H, s), 6.83 (2H, d, J=10 Hz), 7.61 (1H, s), 8.21 (2H, d, J=10 Hz), 8.88 (2H, s)

EXAMPLE 61

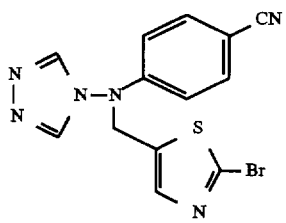

4-[N-[(2-bromothiazol-5-yl)methyl]-N-(4-cyanophenyl) amino]-4H-1,2,4-triazole

Starting Compounds: 4-(4-cyanophenyl)amino-4H-1,2,4-triazole and 2-bromo-5-(bromomethyl)thiazole Elementary Analysis (for $C_{13}H_9N_6SBr$)

|  | C (%) | H (%) | N (%) | Br (%) | S (%) |
|---|---|---|---|---|---|
| Calculated: | 43.23 | 2.51 | 23.27 | 22.12 | 8.88 |
| Measured: | 43.08 | 2.41 | 23.27 | 22.27 | 8.75 |

Mass Spectrometry (m/z): 362 ($M^+$)

Nuclear Magnetic Resonance Spectrum (DMSO-$d_6$, TMS internal standard)

δ: 5.36 (2H, s), 6.79 (2H, d, J=9 Hz) 7.58 (1H, s), 7.79 (2H, d, J=9 Hz), 8.84 (2H, s)

EXAMPLE 62

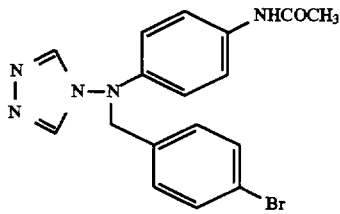

0.28 Milliliter of acetic anhydride was added to ml of a pyridine solution containing 0.35 g of 4-[N-(4-aminophenyl)-N-(4-bromobenzyl)amino]-4H-1,2,4-triazole at room temperature and the mixture was stirred for about minutes. After reaction, the solvent was removed by distillation under reduced pressure, and a proper amount of an aqueous sodium hydrogen carbonate solution was added to the resulting residue, which was then extracted with ethyl acetate. The ethyl acetate layer was washed with water and dried over anhydrous magnesium sulfate, and the solvent was removed by distillation under reduced pressure. The residue was purified by silica gel chromatography to obtain 0.33 g of 4-[N-(4-acetylaminophenyl)-N-(4-bromobenzyl)amino]-4H-1,2,4-triazole from the chloroform/methanol (50/1) eluate.

Elementary Analysis (for $C_{17}H_{16}N_5OBr$)

|  | C (%) | H (%) | N (%) |
|---|---|---|---|
| Calculated: | 52.86 | 4.18 | 18.13 |
| Measured: | 52.85 | 4.22 | 18.24 |

Mass Spectrometry (m/z): 387 ($M^+$+1)

Nuclear Magnetic Resonance Spectrum (DMSO-$d_6$, TMS internal standard)

δ: 2.01 (3H, s), 4.86 (2H, s), 6.78 (2H, d, J=9.0 Hz), 7.27 (2H, d, J=8.6 Hz), 7.51 (4H, d, J=9.0 Hz), 8.75 (2H, s), 9.88 (1H, br)

EXAMPLE 63

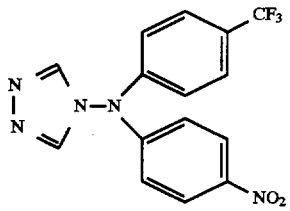

0.23 Gram of 4-[(4-trifluoromethylphenyl)-amino]-4H-1,2,4-triazole was added little by little to an N,N-dimethylformamide suspension of 0.04 g of sodium hydride at room temperature. The mixture was stirred for 30 minutes at room temperature, and 0.15 g of 4-fluoronitrobenzene was added thereto and the mixture was stirred for 15 minutes at 100° C. The solvent was removed by distillation under reduced pressure and water was added to the residue, which was then extracted with chloroform. The chloroform layer was washed with water and dried over anhydrous magnesium sulfate, and the solvent was removed by distillation. The crystals thus obtained were recrystallized from a mixed solvent of ethyl acetate/ether to give 280 mg of 4-[N-(4-nitrobenzyl)-N-(4-trifluoromethylphenyl)amino]-4H-1,2,4-triazole.

Elementary Analysis (for $C_{15}H_{10}N_5O_2$)

|  | C (%) | H (%) | N (%) | F (%) |
|---|---|---|---|---|
| Calculated: | 51.58 | 2.89 | 20.05 | 16.32 |
| Measured: | 51.58 | 2.84 | 20.11 | 16.22 |

Nuclear Magnetic Resonance Spectrum (CDCl$_3$, TMS internal standard)

δ: 6.90 (2H, d, J=9 Hz), 7.24 (2H, d, J=8 Hz), 7.72 (2H, d, J=8 Hz), 8.22 (2H, d, J=9 Hz), 8.47 (2H, s)

In the same manner as in Example 53, the following compounds were obtained.

EXAMPLE 64

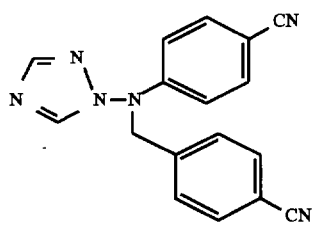

1-[N-(4-cyanobenzyl)-N-(4-cyanophenyl)amino]-1H-1,2,4-triazole

Starting Compounds: 1-[N-(4-cyanophenyl)amino]-1H-1,2,4-triazole and 4-cyanobenzyl bromide Elementary Analysis (for $C_{17}H_{12}N_6$)

|  | C (%) | H (%) | N (%) |
|---|---|---|---|
| Calculated: | 67.99 | 4.03 | 27.98 |
| Measured: | 67.94 | 4.17 | 27.99 |

Mass Spectrometry (m/z): 300 ($M^+$)

Nuclear Magnetic Resonance Spectrum (DMSO-$d_6$, TMS internal standard)

δ: 5.18 (2H, s), 6.70 (2H, d, J=9 Hz), 7.61 (2H, d, J=9 Hz), 7.75 (2H, d, J=9 Hz), 7.82 (2H, d, J=9 Hz), 8.19 (1H, s), 8.77 (1H, s)

EXAMPLE 65

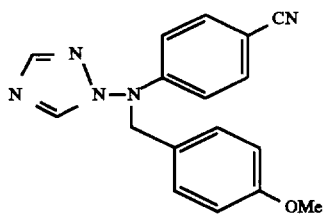

1-[N-(4-cyanophenyl)-N-(4-methoxybenzyl)amino]-1H-1,2,4-triazole

Starting Compounds: 1-[N-(4-cyanophenyl)amino]-1H-1,2,4-triazole and 4-methoxybenzyl chloride Elementary Analysis (for $C_{17}H_{15}N_5O$)

|  | C (%) | H (%) | N (%) |
|---|---|---|---|
| Calculated: | 66.87 | 4.95 | 22.94 |
| Measured: | 66.88 | 5.09 | 22.92 |

Mass Spectrometry (m/z): 305 ($M^+$)

Nuclear Magnetic Resonance Spectrum (DMSO-$d_6$, TMS internal standard)

δ: 3.72 (3H, s), 4.93 (2H, s), 6.77 (2H, d, J=9 Hz), 6.85 (2H, d, J=9 Hz), 7.23 (2H, d, J=9 Hz), 7.74 (2H, d, J=9 Hz), 8.15 (1H, s), 8.53 (1H, s)

EXAMPLE 66

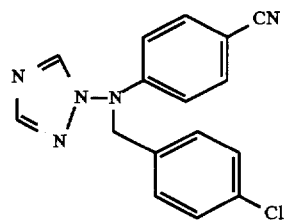

1-[N-(4-chlorobenzyl)-N-(4-cyanophenyl)amino]-1H-1,2,4-triazole

Starting Compounds: 1-[N-(4-cyanophenyl)amino]-1H-1,2,4-triazole and 4-chlorobenzyl chloride Elementary Analysis (for $C_{16}H_{12}N_5Cl$)

|  | C (%) | H (%) | N (%) | Cl (%) |
|---|---|---|---|---|
| Calculated: | 62.04 | 3.90 | 22.61 | 11.45 |
| Measured: | 61.85 | 3.94 | 22.64 | 11.53 |

Mass Spectrometry (m/z): 309 ($M^+$)

Nuclear Magnetic Resonance Spectrum (DMSO-$d_6$, TMS internal standard)

δ: 5.05 (2H, s), 6.74 (2H, d, J=9 Hz), 7.38 (4H, s), 7.75 (2H, d, J=9 Hz), 8.17 (1H, s), 8.66 (1H, s)

EXAMPLE 67

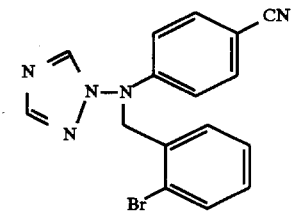

1-[N-(2-bromobenzyl)-N-(4-cyanophenyl)amino]-1H-1,2,4-triazole

Starting Compounds: 1-[N-(4-cyanophenyl)amino]-1H-1,2,4-triazole and 2-bromobenzyl bromide Elementary Analysis (for $C_{16}H_{12}N_5Br$)

|  | C (%) | H (%) | N (%) | Br (%) |
|---|---|---|---|---|
| Calculated: | 54.25 | 3.41 | 19.77 | 22.56 |
| Measured: | 54.05 | 3.42 | 19.78 | 22.66 |

Mass Spectrometry (m/z): 353 ($M^+$)

Nuclear Magnetic Resonance Spectrum (DMSO-$d_6$, TMS internal standard)

δ: 5.10 (2H, s), 6.76 (2H, d, J=9 Hz), 7.24–7.34 (3H, m), 7.66 (1H, dd, J=1 Hz, 8 Hz), 7.71 (2H, d, J=9 Hz), 8.17 (1H, s), 8.56 (1H, s)

EXAMPLE 68

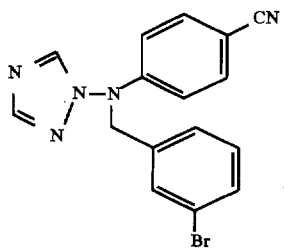

1-[N-(3-bromobenzyl)-N-(4-cyanophenyl)amino]-1H-1,2,4-triazole

Starting Compounds: 1-[N-(4-cyanophenyl)amino]-1H-1,2,4-triazole and 3-bromobenzyl bromide Elementary Analysis (for $C_{16}H_{12}N_5Br$)

|  | C (%) | H (%) | N (%) | Br (%) |
|---|---|---|---|---|
| Calculated: | 54.25 | 3.41 | 19.77 | 22.56 |
| Measured: | 54.08 | 3.41 | 19.78 | 22.64 |

Mass Spectrometry (m/z): 353 ($M^+$)

Nuclear Magnetic Resonance Spectrum (DMSO-$d_6$, TMS internal standard)

δ: 5.07 (2H, s), 6.72 (2H, d, J=9 Hz), 7.29 (1H, t, J=8 Hz), 7.38 (1H, d, J=8 Hz), 7.49 (1H, d, J=8 Hz), 7.61 (1H, s), 7.75 (2H, d, J=9 Hz), 8.19 (1H, s), 8.74 (1H, s)

EXAMPLE 69

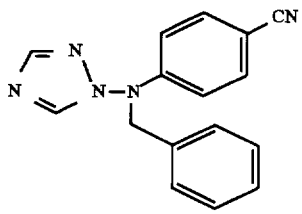

1-[N-benzyl-N-(4-cyanophenyl)amino]-1H-1,2,4-triazole

Starting Compounds: 1-[N-(4-cyanophenyl)amino]-1H-1,2,4-triazole and benzyl bromide Elementary Analysis (for $C_{16}H_{13}N_5$)

|  | C (%) | H (%) | N (%) |
|---|---|---|---|
| Calculated: | 69.80 | 4.76 | 25.44 |
| Measured: | 69.72 | 4.81 | 25.41 |

Mass Spectrometry (m/z): 275 ($M^+$)

Nuclear Magnetic Resonance Spectrum (DMSO-$d_6$, TMS internal standard)

δ: 5.03 (2H, s), 6.75 (2H, d, J=9 Hz), 7.28–7.36 (5H, m), 7.75 (2H, d, J=9 Hz), 8.16 (1H, s), 8.62 (1H, s)

EXAMPLE 70

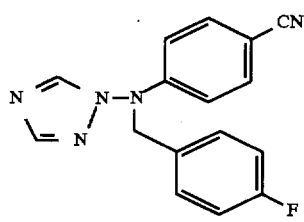

1-[N-(4-fluorobenzyl)-N-(4-cyanophenyl)amino]-1H-1,2,4-triazole

Starting Compounds: 1-[N-(4-cyanophenyl)amino]-1H-1,2,4-triazole and 4-fluorobenzyl bromide Elementary Analysis (for $C_{16}H_{12}N_5F$)

|  | C (%) | H (%) | N (%) | F (%) |
|---|---|---|---|---|
| Calculated: | 65.52 | 4.12 | 23.88 | 6.48 |
| Measured: | 65.60 | 4.23 | 23.83 | 6.47 |

Mass Spectrometry (m/z): 293 ($M^+$)

Nuclear Magnetic Resonance Spectrum (DMSO-$d_6$, TMS internal standard)

δ: 5.02 (2H, s), 6.76 (2H, d, J=9 Hz), 7.03–7.47 (4H, m), 7.75 (2H, d, J=9 Hz), 8.15 (1H, s), 8.60 (1H, s)

EXAMPLE 71

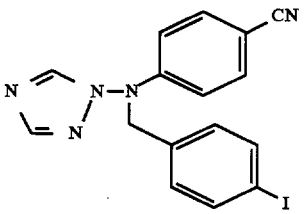

1-[N-(4-cyanophenyl)-N-(4-iodobenzyl)amino]-1H-1,2,4-triazole

Starting Compounds: 1-[N-(4-cyanophenyl)amino]-1H-1,2,4-triazole and 4-iodobenzyl chloride Elementary Analysis (for $C_{16}H_{12}N_5I$)

|  | C (%) | H (%) | N (%) | I (%) |
|---|---|---|---|---|
| Calculated: | 47.90 | 3.01 | 17.46 | 31.63 |
| Measured: | 47.62 | 3.00 | 17.50 | 31.71 |

Mass Spectrometry (m/z): 401 ($M^+$)

Nuclear Magnetic Resonance Spectrum (CDCl$_3$, TMS internal standard)

δ: 4.85 (2H, s), 6.69 (2H, d, J=7 Hz), 7.01 (2H, d, J=8 Hz), 7.52–7.71 (4H, m), 7.87 (1H, s), 8.02 (1H, s)

EXAMPLE 72

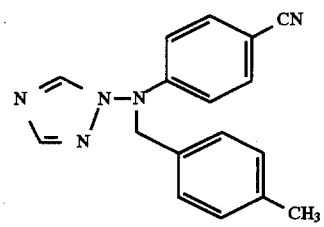

1-[N-(4-cyanophenyl)-N-(4-methylbenzyl)amino]-1H-1,2,4-triazole

Starting Compounds: 1-[N-(4-cyanophenyl)amino]-1H-1,2,4-triazole and α-bromo-p-xylene Elementary Analysis (for $C_{17}H_{15}N_5$)

|  | C (%) | H (%) | N (%) |
|---|---|---|---|
| Calculated: | 70.57 | 5.23 | 24.20 |
| Measured: | 70.46 | 5.28 | 24.12 |

Mass Spectrometry (m/z): 289 ($M^+$)

Nuclear Magnetic Resonance Spectrum ($CDCl_3$, TMS internal standard)

δ: 2.32 (3H, s), 4.85 (2H, s), 6.71 (2H, d, J=7 Hz), 7.11 (4H, s), 7.56 (2H, d, J=7 Hz), 7.80 (1H, s), 8.01 (1H, s)

EXAMPLE 73

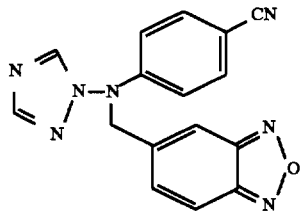

5-[[N-(4-cyanophenyl)-N-(1H-1,2,4-triazol-1-yl)-amino]methyl]benzofurazan

Starting Compounds: 1-[N-(4-cyanophenyl)amino]-1H-1,2,4-triazole and 5-bromomethylbenzofurazan Elementary Analysis (for $C_{16}H_{11}N_7O$)

|  | C (%) | H (%) | N (%) |
|---|---|---|---|
| Calculated: | 60.56 | 3.49 | 30.90 |
| Measured: | 60.51 | 3.53 | 30.88 |

Mass Spectrometry (m/z): 317 ($M^+$)

Nuclear Magnetic Resonance Spectrum (DMSO-$d_6$, TMS internal standard)

δ: 5.26 (2H, s), 6.75 (2H, d, J=9 Hz), 7.68 (1H, d, J=9 Hz), 7.77 (2H, d, J=9 Hz), 8.03 (1H, s), 8.08 (1H, d, J=9 Hz), 8.22 (1H, s), 8.89 (1H, s)

EXAMPLE 74

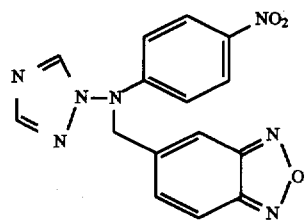

5-[[N-(4-nitrophenyl)-N-(1H-1,2,4-triazol-1-yl)-amino]methyl]benzofurazan

Starting Compounds: 1-[N-(4-nitrophenyl)amino]-1H-1,2,4-triazole and 5-bromomethylbenzofurazan Elementary Analysis (for $C_{15}H_{11}N_7O_3$)

|  | C (%) | H (%) | N (%) |
|---|---|---|---|
| Calculated: | 53.41 | 3.29 | 29.07 |
| Measured: | 53.29 | 3.32 | 29.16 |

Mass Spectrometry (m/z): 337 ($M^+$)

Nuclear Magnetic Resonance Spectrum (DMSO-$d_6$, TMS internal standard)

δ: 5.33 (2H, s), 6.78 (2H, d, J=9 Hz), 7.70 (1H, d, J=9 Hz), 8.07 (1H, s), 8.10 (1H, d, J=9 Hz), 8.20 (2H, d, J=9 Hz), 8.26 (1H, s), 8.95 (1H, s)

EXAMPLE 75

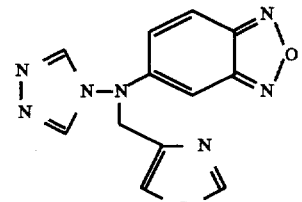

5-[N-(4-thiazolylmethyl)-N-(4H-1,2,4-triazol-4-yl)-amino]benzofurazan

Starting Compounds: 5-[N-(4H-1,2,4-triazol-4-yl)-amino]benzofurazan and 4-chloromethylthiazole Elementary Analysis (for $C_{10}H_9N_7OS$)

|  | C (%) | H (%) | N (%) | S (%) |
|---|---|---|---|---|
| Calculated: | 48.15 | 3.03 | 32.76 | 10.71 |
| Measured: | 48.05 | 3.05 | 32.72 | 10.60 |

Mass Spectrometry (m/z): 299 ($M^+$)

Nuclear Magnetic Resonance Spectrum (DMSO-$d_6$, TMS internal standard)

δ: 5.26 (2H, s), 7.04–7.06 (2H, m), 7.75 (1H, s) 8.01 (1H, d, J=9 Hz), 8.77 (2H, s), 9.11 (1H, s)

Formulation of Oral Preparation:

|  | Content (mg) |
|---|---|
| Tablet Core |  |
| Compound of Example 15 | 1.0 |
| Lactose | 76.4 |

| | Content (mg) |
|---|---|
| Corn Starch | 19.3 |
| Hydroxypropylcellulose | 3.0 |
| Magnesium Stearate | 0.3 |
| Subtotal | 100 |
| Tablet Coat | |
| Hydroxypropyl Methylcellulose 2910 | 2.9 |
| Polyethylene Glycol 6000 | 0.4 |
| Titanium Dioxide | 1.6 |
| Talc | 0.1 |
| Subtotal | 5 |
| Total | 105 |

Preparation of 1 mg-tablet:

7 Grams of the compound of Example 15 and 534.8 g of lactose were blended in a polyethylene bag. The mixture was mixed and milled in a sample mill (manufactured by Hosokawa Micron Co.). 541.8 Grams of the milled mix and 135.1 g of corn starch were uniformly blended with a fluid granulating coating device (manufactured by Ohkawara Manufacturing Co.). To this was sprayed 210 g of 10% hydroxypropyl cellulose solution for granulation. After being dried, the granules formed were passed through a 20-mesh sieve, to which 2.1 g of magnesium stearate was added. These were formed into 100 mg-weight tablets with a rotary tabletting machine (manufactured by Hata Ironworks Co.) using a mortar-pounder of 6.5 mmφ×7.8 R. 350 Grams of a coating liquid containing 20.3 g of hydroxypropyl methylcellulose, 2.8 g of polyethylene glycol 6000, 11.2 g of titanium dioxide and 0.7 g of talc was sprayed over the tablets (100 mg/tablet) in a coating device (manufactured by Freund Industrial Co.) to form film-coated tablets each with a coat of 5 mg/tablet.

What is claimed is:

1. A triazolyl-substituted tertiary amino compound of formula (I):

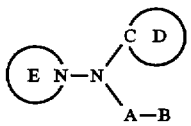

wherein A represents a single bond, a methylene, ethylene or carbonyl group;

B represents a lower alkyl group, an unsubstituted aryl group, a mono-substituted aryl group wherein when the substituent on said aryl group is a halogen atom it is selected from the group consisting of fluorine, bromine and iodine, an optionally substituted 5- or 6-membered heterocyclic group having a hetero ring with from 1 to 3 hetero atoms of oxygen, sulfur and/or nitrogen, or an optionally substituted bicyclic fused heterocyclic group composed of said heterocyclic group and a benzene group;

the D ring represents an optionally substituted aryl group, an optionally substituted 5- or 6-membered heterocyclic group having from 1 to 2 hetero atoms of oxygen, sulfur and/or nitrogen, or an optionally substituted bicyclic fused heterocyclic group composed of said hetero ring and a benzene ring; and and the E ring represents a 4H-1,2,3-triazole ring, a 1H-1,2,4-triazole ring or a 1-H-1,2,3-triazole ring;

or a salt thereof.

2. 4-[N-(4-Bromobenzyl)-N-(4-cyanophenyl)-amino]4H-1,2,4-triazole or a salt thereof.

3. 4-[N-(4-Bromobenzyl)-N-(4-nitrophenyl)-amino]4H-1,2,4-triazole or a salt thereof.

4. The compound or a salt thereof as claimed in claim 1, wherein the D ring is an unsubstituted or substituted aryl group.

5. An aromatase inhibitor comprising, as an active ingredient, a triazolyl-substituted tertiary amino compound of formula (I) or a salt thereof as claimed in claim 1.

6. A aromatase inhibitor according to claim 5, wherein an active ingredient is 4-[N-(4-Bromobenzyl)-N-(4-cyanophenyl)-amino]4H-1,2,4-triazole or a salt thereof.

7. A aromatase inhibitor according claim 5, wherein an active ingredient is 4-[N-(4-Bromobenzyl)-N-(4-nitrophenyl)-amino]4H-1,2,4-triazole or a salt thereof.

8. A pharmaceutical composition comprising, as an active ingredient, a triazolyl-substituted tertiary amino compound of formula (I) or a salt thereof as claimed in claim 1, and a pharmaceutically acceptable carrier.

9. A pharmaceutical composition according to claim 8, wherein an active ingredient is 4-[N-(4-Bromobenzyl)-N-(4-cyanophenyl)-amino]4H-1,2,4-triazole or a salt thereof.

10. A Pharmaceutical composition according to claim 8, wherein an active ingredient is 4-[N-(5-Bromobenzyl)-N-(4-nitrophenyl)-amino]4H-1,2,4-triazole or a salt thereof.

* * * * *